(12) United States Patent
Bennett et al.

(10) Patent No.: US 7,687,501 B2
(45) Date of Patent: Mar. 30, 2010

(54) PYRIDOTHIENOPYRIDAZINONE DERIVATIVES AS MGLUR1 ANTAGONISTS

(75) Inventors: Chad E. Bennett, Metuchen, NJ (US); William J. Greenlee, Teaneck, NJ (US); Chad E. Knutson, Garwood, NJ (US); Duane A. Burnett, Bernardsville, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/505,140

(22) Filed: Aug. 16, 2006

(65) Prior Publication Data

US 2007/0072864 A1    Mar. 29, 2007

Related U.S. Application Data

(60) Provisional application No. 60/709,562, filed on Aug. 19, 2005.

(51) Int. Cl.
| | |
|---|---|
| C07D 495/14 | (2006.01) |
| C07D 417/14 | (2006.01) |
| A61K 31/4985 | (2006.01) |
| C07D 213/85 | (2006.01) |
| C07D 495/04 | (2006.01) |
| C07D 239/30 | (2006.01) |
| C07D 239/58 | (2006.01) |
| A61P 25/06 | (2006.01) |
| A61P 25/04 | (2006.01) |
| A61P 25/22 | (2006.01) |
| A61P 25/28 | (2006.01) |

(52) U.S. Cl. ............. 514/248; 544/234; 544/334; 544/319; 546/288; 546/114

(58) Field of Classification Search ........... 514/217.05, 514/248; 540/481, 476; 544/234
See application file for complete search history.

(56) References Cited

U.S. PATENT DOCUMENTS

| 5,945,417 | A | 8/1999 | Olesen et al. | |
|---|---|---|---|---|
| 6,872,743 | B2 * | 3/2005 | Beight et al. | 514/410 |
| 7,235,554 | B2 * | 6/2007 | Froissant et al. | 514/248 |
| 2007/0049593 | A1 * | 3/2007 | Oka et al. | 514/243 |
| 2007/0072863 | A1 * | 3/2007 | Bennett et al. | 514/248 |
| 2007/0219202 | A1 * | 9/2007 | Froissant et al. | 514/248 |

FOREIGN PATENT DOCUMENTS

| EP | 0 512 817 A1 | 11/1992 |
|---|---|---|
| JP | 2002-308882 | 10/2002 |

OTHER PUBLICATIONS

Moré, et al., Behav. Pharmacol. Jul. 2007;18(4):273-81.*
Nagaraja, et al., Naunyn-Schmiedeberg's Arch. Pharmacol. (2004) 370: 26-34.*
Pietraszek, et al., Amino Acids (2007) 32:173-178.*
El-Kouhen, et al., Brit. J. Pharmacol. (2006) 149(6), p. 761-774.*
Murotomi, et al., J. Neurochem., 2008, 105, pp. 1625-1634.*
Pietraszek, et al. (Pietraszek II), Neuropharmacol., vol. 49 #1, Jul. 2005, pp. 73-85.*
Zheng G.Z. et al., "Structure—Activity Relationship of Triazafluorenone Derivatives as Potent and Selective mGluR1 Antagonists", Journal of Medicinal Chemistry, American Chemical Society. vol. 48, No. 23, 2005, pp. 7374-7388.
International Search Report for PCT/US 2006/031944 for CN06343US01, Feb. 13, 2007—5 Pages.

* cited by examiner

*Primary Examiner*—James O. Wilson
*Assistant Examiner*—Cecilia M Jaisle
(74) *Attorney, Agent, or Firm*—Krishna G. Bannerjee; Kenrick L. Vidale; Keith D. MacMillan

(57) ABSTRACT

In its many embodiments, the present invention provides tricyclic compounds of formula I (wherein $J^1$-$J^3$, X, Z, and $R^1$, $R^3$, and $R^4$ are as defined herein) useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptor (e.g., mGluR1) such as, for example, pain, migraine, anxiety, urinary incontinence and neurodegenerative diseases such Alzheimer's disease.

formula I

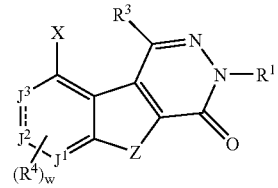

32 Claims, No Drawings

PYRIDOTHIENOPYRIDAZINONE DERIVATIVES AS MGLUR1 ANTAGONISTS

This Application claims the benefit of U.S. Provisional Application Ser. No. 60/709,562, filed Aug. 19, 2005, which is incorporated herein by reference in its entirety.

FIELD OF THE INVENTION

The present invention relates to fused tricyclic compounds useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptor (e.g., mGluR1) such as, for example, pain, migraine, anxiety, urinary incontinence and neurodegenerative diseases such as Alzheimer's disease.

BACKGROUND OF THE INVENTION

Glutamate is an important excitatory neurotransmitter in the mammalian central nervous system. Glutamate synaptic responses in the central nervous system (CNS) are mediated via activation of two families of receptors: ligand-gated cation channels, referred to as ionotropic glutamate receptors, and G-protein-coupled receptors known as metabotropic glutamate receptors (mGluRs). Thus far, eight mGluR subtypes, together with splice variants, have been cloned and characterized in functional studies (Schoepp et al. *Neuropharmacology*, 1999, 38, 1431-1476). The eight mGluRs are grouped into three classes based on structural homology, pharmacology, and signal transduction mechanisms.

Group I receptors (mGluR1 and mGluR5) couple through $G_q/_{11}$ proteins to the activation of phospholipase C (PLC) resulting in phosphoinositide (PI) hydrolysis, the release of calcium from intracellular stores. While group 11 (mGluR2 and mGluR3) and III (mGluR4, mGluR6 mGluR7 and mGluR8) are negatively coupled to adenyl cyclase (AC) through $G_i/G_o$ proteins thereby inhibiting cyclic AMP (cAMP) formation (A. Francesconi and R. M. Duvoisin, *J. Biol. Chem.* 1998, 273(10), 5615-5624).

Glutamate and Pain

Chronic pain is an area of high unmet medical need. Current therapies are not adequate and chronic pain is often refractory to most commonly used analgesics, including opioids. Glutamate plays a major role in nociceptive processing. Glutamate receptors, including mGluRs, are expressed in relevant areas of the brain, spinal cord and periphery that are involved in pain sensation and transmission.

Chronic pain may be due to tissue injury and diseases (inflammatory pain) or to the central and peripheral nervous system (neuropathic pain) and is associated with severe chronic sensory disturbances characterized by spontaneous pain, hyperalgesia (exaggerated responsiveness to painful stimuli) and allodynia (wrong perception of non-noxious stimuli as painful). Prevalent symptoms in human patients include cold hyperalgesia, mechanical allodynia and, less commonly, heat hyperalgesia.

Chronic pain is a true disease. It is believed to be a result of the plasticity at synapses in nociceptive processing centers, a phenomenon referred to as "central sensitization" which consists of increased excitability of spinal cord dorsal horn neurons. Glutamate receptors have been identified for their key role in central sensitization. Plasticity at synapses involved in nociceptive processing requires activation of ionotropic glutamate receptors such as NMDA and this plasticity is modulated by mGluRs including mGluR1. NMDA receptor antagonists have been tested in experimental therapies for the prevention and treatment of persistent pain following injury. However, there are significant undesiderable side effects associated with the use of NMDA antagonists due largely to the critical role of those receptors in normal excitatory synaptic transmission throughout the nervous system. These side effects include psychosis, hyperactivity, fatigue, dizziness, and in the case of higher levels of NMDA antagonists, amnesia and neuronal toxicity. Drugs designed to antagonize mGluR1 receptors are expected to have less side effect liability since they appear to selectively modulate the pathologically abnormal spinal NMDA receptor activation associated with persistent pain states whilst having little effect on the normal spinal synaptic processes involved in non-painful sensory perception. Thus, mGluR antagonists might perform well clinically in chronic pain states because they avoid the side effects inherent to widespread spinal and supraspinal NMDA receptor antagonism.

mGluR1 and Pain

A number of behavioral (Fisher et al. *Neuroreport*, 1998, 20, 1169-1172; Fundytus et al. *Neuroreport*, 1998, 9, 731-735; Bhave et al. *Nature Neurosci.*, 2001, 4, 417-423; Dolan et al. *Neuropharmacology*, 2002, 43, 319-326; Dolan et al. *Pain*, 2003, 106, 501-512) and electrophysiological (Young et al. *Neuropharmacology*, 1994, 33, 141-144; and Young et al. *Brain Res.*, 1997, 777, 161-169) studies have demonstrated a specific role for Group I mGluRs, and in particular mGluR1 receptors, in nociceptive processing in the CNS, including mechanisms of hyperalgesia and inflammation. In the spinal cord, mGluR1 appears to be localized primarily on postsynaptic elements throughout the dorsal and ventral horns. (Neugebauer, *Trends Neurosci.*, 2001, 24, 550-552). The intrinsic activation of spinal mGluR1 in chronic nociception has been demonstrated using antagonists, antibodies and antisense oligonucleotides. Intrathecal administration of an mGluR1 antagonist produced antinociceptive effects in the second phase of formalin-induced nociceptive behavior (Neugebauer, *Trends Neurosci.*, 2001, 24, 550-552). Behavioral studies have also addressed the role of spinal mGluR1 receptors in the spinal injury and ligation models of neuropathic pain. Expression of mGluR1 is increased in rats following spinal cord injury and this may mediate the chronic central pain induced by the injury (Mills and Hulsebosch, *Neurosci. Lett.*, 2002, 319, 59-62). Knockdown of spinal mGluR1 by intrathecal infusion of antisense oligonucleotides attenuated cold hyperalgesia and mechanical allodynia in neuropathic rats (Fundytus et al. *Br. J. Pharmacol.*, 2001, 132, 354-367; and Fundytus et al. *Pharmacol. Biochem. Behav.*, 2002, 73, 401-410). Additionally, spinal administration of anti-mGluR1 IgG antibodies reduced cold hyperalgesia, but not mechanical allodynia, in neuropathic rats (Fundytus et al. *Neuroreport*, 1998, 9, 731-735). The critical role of spinal mGluR1 receptors in pain-related central sensitization is emphasized at the single cell level by electrophysiological in vivo studies in anesthetized animals. Intraspinal administration of an mGluR1 antagonist inhibited the responses of primate spinothalamic tract neurons to brief noxious, but not innocuous, mechanical cutaneous stimuli, as well as central sensitization in the capsaicin pain model (Neugebauer et al. *J. Neurophysiol.*, 1999, 82, 272-282). In rats with knocked down mGluR1 expression, the responses of multireceptive dorsal horn neurons to noxious input evoked by repeated topical applications of the C-fiber irritant mustard oil were significantly reduced compared to control neurons; the

SUMMARY OF THE INVENTION

In its many embodiments, the present invention provides a novel class of tricyclic compounds useful as metabotropic glutamate receptor (mGluR) antagonists, particularly as selective mGluR1 antagonists, pharmaceutical compositions comprising one or more such compounds, methods of preparing pharmaceutical formulations comprising one or more such compounds, and methods of treatment, prevention, inhibition or amelioration of one or more diseases associated with the mGluRs, particularly mGluR1, using such compounds or pharmaceutical compositions.

In one aspect, the present application discloses a compound of formula I:

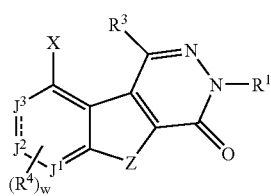

formula I or a pharmaceutically acceptable salt or solvate thereof, wherein:

$J^1$, $J^2$, and $J^3$ are independently N or C, provided that 1-2 of $J^1$, $J^2$, and $J^3$ are N;

----- is a single or double bond;

$R^1$ is selected from the group consisting of H, —$NR^5R^6$, —$OR^6$, —$SR^6$, —CN, —$C(O)R^6$, —$C(O_2)R^6$, —$OC(O)R^6$, —$C(O)NR^6R^7$, —$N(R^6)C(O)R^6$, —$S(O_2)NR^6R^7$ —$N(R^6)S(O_2)R^6$, —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$, or wherein said $R^1$ aryl may optionally be substituted with two radicals on adjacent carbon atoms, which radicals are taken together with the carbon atoms to which they are attached to form a five to six membered heterocyclyl or heteroaryl ring which ring is optionally substituted one at least one $R^8$;

X is selected from the group consisting of H, —$NR^5R^6$, —$SR^7$, —$NR^2NR^5R^6$, —$C(O)R^6$, —$SO_2R^7$, —$C(O)NR^6R^7$, and alkyl, alkoxy, alkenyloxy, alkynyl, cycloalkyl, cycloalkoxy, aryloxy, arylalkyl, heteroaryl, heteroarylalkyl, heterocyclyl, and heterocyclylalkyl groups optionally substituted with at least one $R^8$;

Z is selected from the group consisting of S, O, and $NR^5$;

$R^3$ is selected from the group consisting of H, halo, —CN, —$NO_2$, —$OR^7$, —$SR^6$, —$NR^5R^6$, —$C(O)R^7$, —$C(O_2)R^7$, —$OC(O)R^6$, —$C(O)NR^6R^7$, —$N(R^6)C(O)R^6$, —$OS(O_2)R^6$, —$S(O_2)R^6$, —$S(O_2)NR^5R^6$, —$N(R^2)S(O_2)R^6$, and —$N(R^2)C(O)NR^5R^6$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^4$ is independently selected from the group consisting of H, halo, —CN, —$NHC(O)R^7$, —$NHSO_2R^{11}$, —$NR^5R^6$, —$OR^7$, —$C(O)R^7$, —$C(O_2)R^7$, —$C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$; or, when w=2, two $R^4$ together with the carbon atoms to which they are attached form a group of the formula:

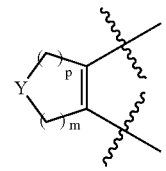

where m and p are each an integer ranging from 0-4, provided that (m+p)=2-7, and Y is selected from the group consisting of S, S(O), $S(O)_2$, O, $NR^5$, $C(R^2)_2$, and C(O);

w is an integer ranging from 1-2;

$R^2$ is selected from the group consisting of H, and alkyl;

$R^5$ is selected from the group consisting of H, —$C(O)R^6$, —$SO_2R^7$, —$C(O)NR^6R^7$, and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$;

$R^6$ and $R^7$ are independently selected from the group consisting of H and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

$R^8$ is selected from the group consisting of H, halo, —$OR^9$, —$NO_2$, —CN, —$NR^9C(O)R^{10}$, —$NR^9SO_2R^{11}$, —$NR^9R^{10}$, —$C(O)R^{10}$, —$C(O)NR^9R^{10}$, $C(O)OR^9$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, —CN, —$NO_2$, —$OR^6$, —$SR^6$, —$C(O)R^{10}$, —$NR^9R^{10}$, —$C(O_2)R^9$, —$C(O)NR^9R^{10}$, —$N(R^9)C(O)R^{10}$, —$N(R^6)C(O)NR^9R^{10}$, and —$NR^9SO_2R^{11}$;

$R^9$ and $R^{10}$ are each independently selected from the group consisting of H and alkyl, alkenyl, alkynyl, cycloalkyl, aryl, arylalkyl, heteroaryl, heteroarylalkyl, and heterocyclyl groups optionally substituted with at least one of halo, —CN, —$NO_2$, —$OR^6$, —$SR^6$, —$NR^5R^6$, —$C(O)R^6$, —$C(O_2)R^6$, —$OC(O)R^6$, —$C(O)NR^6R^7$, —$N(R^6)C(O)R^6$, —$OS(O_2)R^6$, —$S(O_2)R^6$, —$S(O_2)NR^5R^6$, —$N(R^6)S(O_2)R^6$, and —$N(R^6)C(O)NR^5R^6$; and $R^{11}$ is selected from the group consisting of alkyl, alkenyl, alkynyl, cycloalkyl, aryl, arylalkyl, heteroaryl, heteroarylalkyl, and heterocyclyl groups optionally substituted with at least one $R^8$.

In another aspect, the present application discloses a compound of formula I, as set forth above, or a pharmaceutically acceptable salt or solvate thereof, wherein:

$J^1$, $J^2$, and $J^3$ are independently N or C, provided that 1-2 of $J^1$, $J^2$, and $J^3$ are N;

----- is a single or double bond;

$R^1$ is selected from the group consisting of H, —$NR^5R^6$, —$OR^6$, —$SR^6$, —CN, —$C(O)R^6$, —$C(O_2)R^6$, —$OC(O)R^6$, —$C(O)NR^6R^7$, —$N(R^6)C(O)R^6$, —$S(O_2)NR^6R^7$ —$N(R^6)S(O_2)R^6$, —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

X is selected from the group consisting of H, $-NR^5R^6$, $-SR^7$, $-NR^2NR^5R^{6,}$ $-C(O)R^6$, $-SO_2R^7$, $-C(O)NR^6R^7$, and alkyl, alkoxy, alkenyl, alkenyloxy, alkynyl, cycloalkyl, cycloalkoxy, aryloxy, arylalkyl, heteroaryl, heteroarylalkyl, heterocyclyl, and heterocyclylalkyl groups optionally substituted with at least one $R^8$;

Z is selected from the group consisting of S, O, and $NR^5$;

$R^3$ is selected from the group consisting of H, halo, $-CN$, $-NO_2$, $-OR^7$, $-SR^6$, $-NR^5R^6$, $-C(O)R^7$, $-C(O_2)R^7$, $-OC(O)R^6$, $-C(O)NR^6R^7$, $-N(R^6)C(O)R^6$, $-OS(O_3R^6$, $-S(O_2)R^6$, $-S(O_2)NR^5R^6$, $-N(R^2)S(O_2)R^6$, and $-N(R^2)C(O)NR^5R^6$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^4$ is independently selected from the group consisting of H, halo, $-CN$, $-NHC(O)R^7$, $-NHSO_2R^{11}$, $-NR^5R^6$, $-OR^7$, $-C(O)R^7$, $-C(O_2)R^7$, $-C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$; or, when w=2, two $R^4$ together with the carbon atoms to which they are attached form a group of the formula:

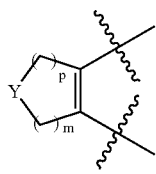

where m and p are each an integer ranging from 0-4, provided that (m+p)=2-7, and Y is selected from the group consisting of S, S(O), S(O)$_2$, O, $NR^5$, $C(R^2)_2$, and C(O);

w is an integer ranging from 1-2;

$R^2$ is selected from the group consisting of H, and alkyl;

$R^5$ is selected from the group consisting of H, $-C(O)R^6$, $-SO_2R^7$, $-C(O)NR^6R^7$, and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$;

$R^6$ and $R^7$ are independently selected from the group consisting of H and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

$R^8$ is selected from the group consisting of H, halo, $-OR^9$, $-NO_2$, $-CN$, $-NR^9C(O)R^{10}$, $-NR^9SO_2R^{11}$, $-NR^9R^{10}$, $-C(O)R^{10}$, $-C(O)NR^9R^{10}$, $C(O)OR^9$, and alkyl alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, $-CN$, $-NO_2$, $-OR^6$, $-SR^6$, $-C(O)R^{10}$, $-NR^9R^{10}$, $-C(O_2)R^9$, $-C(O)NR^9R^{10}$, $-N(R^9)C(O)R^{10}$, $-N(R^6)C(O)NR^9R^{10}$, and $-NR^9SO_2R^{11}$;

$R^9$ and $R^{10}$ are each independently selected from the group consisting of H and alkyl, alkenyl, alkynyl, cycloalkyl, aryl, arylalkyl, heteroaryl, heteroarylalkyl, and heterocyclyl groups optionally substituted with at least one of halo, $-CN$, $-NO_2$, $-OR^6$, $-SR^6$, $-NR^5R^6$, $-C(O)R^6$, $-C(O_2)R^6$, $-OC(O)R^6$, $-C(O)NR^6R^7$, $-N(R^6)C(O)R^6$, $-OS(O_2)R^6$, $-S(O_2)R^6$, $-S(O_2)NR^5R^6$, $-N(R^6)S(O_2)R^6$, and $-N(R^6)C(O)NR^5R^6$, and $R^{11}$ is selected from the group consisting of alkyl, alkenyl, alkynyl, cycloalkyl, aryl, arylalkyl, heteroaryl, heteroarylalkyl, and heterocyclyl groups optionally substituted with at least one $R^8$.

The compounds of formula I are useful as selective metabotropic glutamate receptor 1 antagonists and thus are useful in the treatment and prevention of pain (neurotropic or inflammatory), migraine, anxiety, urinary incontinence and neurodegenerative diseases such as Alzheimer's disease.

DETAILED DESCRIPTION

In one embodiment, the present invention discloses tricyclic compounds which are represented by structural formula I or a pharmaceutically acceptable salt, solvate or ester thereof, wherein the various moieties are as described above.

In one embodiment, in formula I, $-NR^5R^6$ is selected from the group consisting of

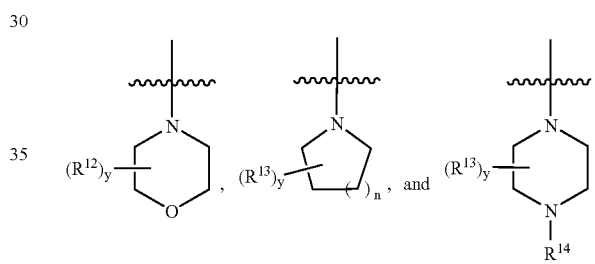

wherein
each $R^{12}$ independently is selected from the group consisting of H, $-CN$, $-C(O)R^6$, $-C(O)OR^7$, $-C(O)NR^6R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;
each $R^{13}$ independently is selected from the group consisting of H, halo, hydroxyl, $-CN$, $-NHC(O)R^7$, $-NHSO_2R^{11}$, $-NR^5R^6$, $-OR^7$, $-C(O)R^6$, $-C(O)OR^7$, $-C(O)NR^6R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;
$R^{14}$ is selected from the group consisting of H, $-C(O)R^6$, $-C(O)OR^7$, $C(O)NR^6R^7$, alkyl, alkenyl, cycloalkyl, aryl, arylalkyl, heteroaryl, heteroarylalkyl, heterocyclyl, and heterocyclylalkyl groups optionally substituted with at least one $R^8$;
n is 0-4; and
y is 1-4.

In another embodiment, in formula I, Z is S, $J^1$ is N, and $J^2$ and $J^3$ are each C.

In another embodiment, in formula I, Z is S, $J^1$ is N, $J^2$ and $J^3$ are each C, and $R^3$ is alkyl.

In another embodiment, in formula I, Z is S, $J^1$ is N, $J^2$ and $J^3$ are each C, and $R^3$ is H.

In another embodiment, in formula I, Z is S, $J^1$ is N, $J^2$ and $J^3$ are each C, and $R^1$ is aryl.

In another embodiment, in formula I, Z is S, $J^1$ is N, $J^2$ and $J^3$ are each C, and $R^1$ is heteroaryl.

In another embodiment, in formula I, Z is S, $J^1$ is N, $J^2$ and $J^3$ are each C, $R^1$ is p-halophenyl, and $R^3$ is H.

In another embodiment, in formula I, X is —$NR^5R^6$. In another embodiment, in formula I, X is —$NR^5R^6$, wherein $R^5$ and $R^6$ are independently selected from the group consisting of hydrogen, and alkyl and cycloalkyl groups optionally substituted with at least one $R^8$.

In another embodiment, in formula I, X is —$NR^5R^6$, wherein $R^5$ and $R^6$ are each alkyl.

In another embodiment, in formula I, X is —$NR^5R^6$, wherein $R^5$ is H and $R^6$ is hydroxyalkyl.

In another embodiment, in formula I, X is —$NR^5R^6$, wherein at least one of $R^5$ and $R^6$ is cycloalkyl.

In another embodiment, in formula I, X is —$NR^5R^6$, $R^5$ is H and $R^6$ is cyclopropyl or cyclobutyl.

In another embodiment, in formula I, X is —$NR^5R^6$, wherein $R^5$ is H and $R^6$ is cyclopropyl.

In another embodiment, in formula I, X is —$NR^5R^6$, wherein —$NR^5R^6$ is

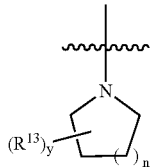

wherein n is 0.

In another embodiment, in formula I, X is —$NR^5R^6$, wherein —$NR^5R^6$ is

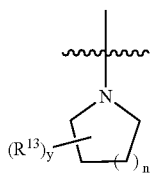

wherein n is 0, wherein $R^{13}$ is H or OH.

In another embodiment, in formula I, X is —$NR^5R^6$, wherein $R^5$ is H and $R^6$ is alkyl which is optionally substituted with at least one substituent selected from the group consisting of —OH, alkoxy, —$CF_3$, and —C≡CH.

In another embodiment, in formula I, X is —$NR^5R^6$, and wherein $R^1$ is selected from the group consisting of cycloalkyl, and aryl, each of which is optionally substituted with at least one $R^8$, or wherein said $R^1$ aryl may optionally contain two radicals on adjacent carbon atoms, which radicals are taken together with the carbon atoms to which they are attached to form a five to six membered heterocyclyl or heteroaryl ring, which is optionally substituted with at least one $R^8$.

In another embodiment, in formula I, X is —$NR^5R^6$, and wherein $R^1$ is selected from the group consisting of cycloalkyl, and aryl, each of which is optionally substituted with at least one $R^8$, or wherein said $R^1$ aryl may optionally contain two radicals on adjacent carbon atoms, which radicals are taken together with the carbon atoms to which they are attached to form a five to six membered heterocyclyl or heteroaryl ring, which is optionally substituted with at least one $R^8$, wherein said $R^1$ cycloalkyl is cyclohexyl.

In another embodiment, in formula I, X is —$NR^5R^6$, and wherein $R^1$ is selected from the group consisting of cycloalkyl, and aryl, each of which is optionally substituted with at least one $R^8$, or wherein said $R^1$ aryl may optionally contain two radicals on adjacent carbon atoms, which radicals are taken together with the carbon atoms to which they are attached to form a five to six membered heterocyclyl or heteroaryl ring, which is optionally substituted with at least one $R^8$, wherein said $R^8$ is selected from the group consisting of alkyl, cycloalkyl, cyano, alkoxy, halo, and hydroxy.

In another embodiment, in formula I, X is —$NR^5R^6$, and wherein $R^1$ is selected from the group consisting of cycloalkyl, and aryl, each of which is optionally substituted with at least one $R^8$, or wherein said $R^1$ aryl may optionally contain two radicals on adjacent carbon atoms, which radicals are taken together with the carbon atoms to which they are attached to form a five to six membered heterocyclyl or heteroaryl ring, which is optionally substituted with at least one $R^8$, wherein said $R^1$ aryl, including $R^1$ aryl containing two radicals on adjacent carbon atoms which are taken together with the carbon atoms to which they are attached to form a five to six membered heterocyclic or heteroaryl ring, is selected from the group consisting of phenyl, and

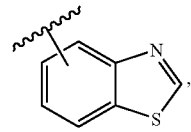

each of which is optionally substituted with at least one $R^8$.

In another embodiment, in formula I, X is —$NR^5R^6$ and $R^1$ is phenyl substituted with at least one $R^8$.

In another embodiment, in formula I, Z is S, $J^1$ and $J^3$ are each N, and $J^2$ is C.

In another embodiment, in formula I, Z is S, $J^1$ and $J^3$ are each N, $J^2$ is C, and $R^3$ is H.

In another embodiment, in formula I, Z is S, $J^1$ and $J^3$ are each N, $J^2$ is C, and $R^1$ is aryl which is optionally substituted.

In another embodiment, in formula I, Z is S, $J^1$ and $J^3$ are each N, $J^2$ is C, and $R^1$ is heteroaryl which is optionally substituted.

In another embodiment, in formula I, Z is S, $J^1$ and $J^3$ are each N, $J^2$ is C, and $R^1$ is p-halophenyl.

In another embodiment, in formula I, Z is S, $J^1$ and $J^3$ are each N, $J^2$ is C, and $R^1$ is p-halophenyl or p-alkoxyphenyl.

In another embodiment, in formula I, Z is S, $J^1$ and $J^3$ are each N, $J^2$ is C, and $R^1$ is cycloalkyl or aryl, each of which is optionally substituted.

In another embodiment, the present invention discloses tricyclic compounds which are represented by structural formulae II-VII or a pharmaceutically acceptable salt, solvate or ester thereof, wherein Z, X, $R^1$, $R^3$, $R^4$, and w are as defined in Formula I:

Formula II

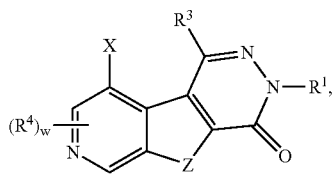

Formula III

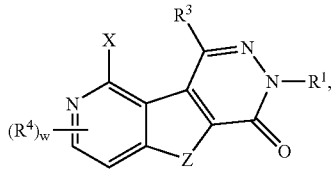

Formula IV

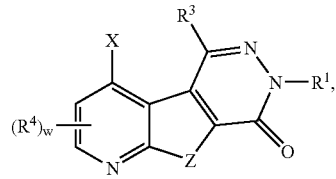

Formula V

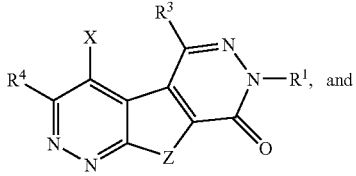

Formula VI

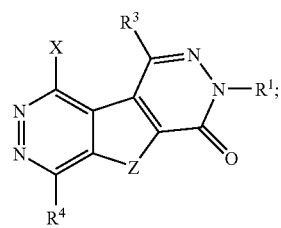, and

Formula VII

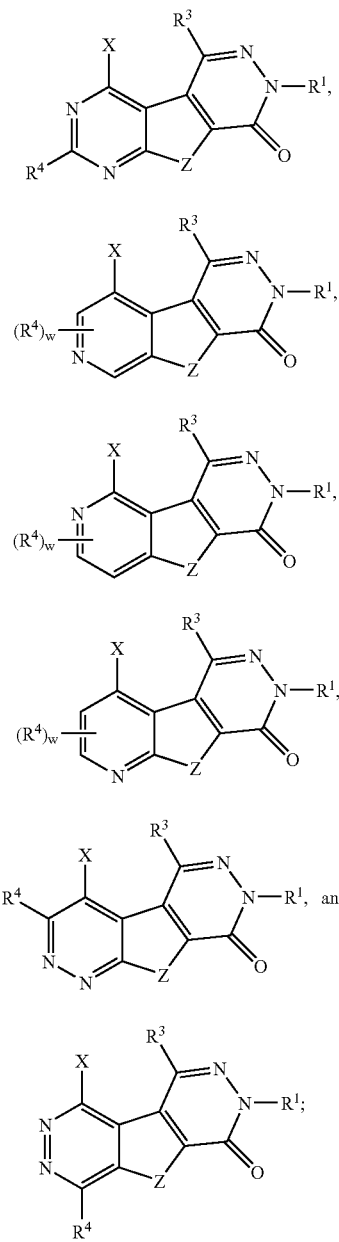

In another embodiment, the present invention discloses tricyclic compounds which are represented by structural formulae II-VI or a pharmaceutically acceptable salt, solvate or ester thereof, wherein Z, X, R¹, R³, R⁴, and w are as defined in Formula I:

Formula II

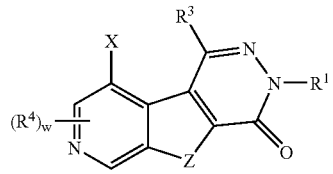

-continued

Formula III

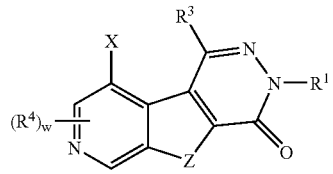

Formula IV

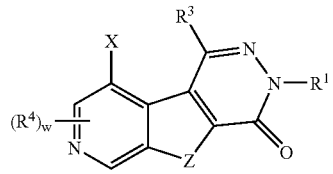

Formula V

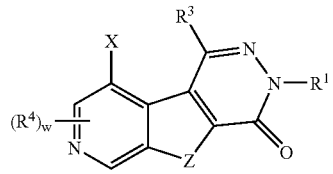

Formula VI

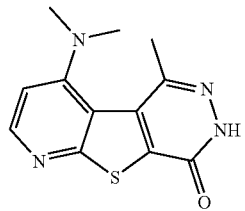

A list of representative compounds of the present invention is shown in Table 1 below.

TABLE 1

| No. | Compound |
|-----|----------|
| 13A | 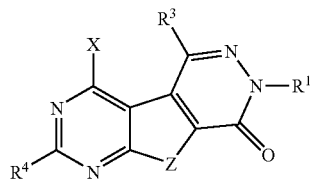 |
| 13B | 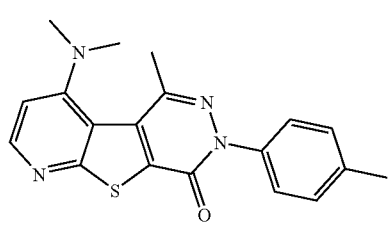 |
| 13C | 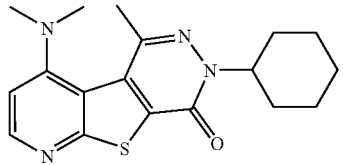 |

TABLE 1-continued

| No. | Compound |
|---|---|
| 13D | |
| 9A | |
| 9C | |
| 9D | |
| 9F | |
| 9B | |
| 9G | |
| 9E | |
| 23D | |
| 21B | |
| 21C | |
| 23A | |
| 23C | |

TABLE 1-continued

| No. | Compound |
|---|---|
| 21A | (structure) |
| 23H | (structure) |
| 23G | (structure) |
| 23E | (structure) |
| 23B | (structure) |
| 23F | (structure) |
| 23I | (structure) |
| 23J | (structure) |
| 23K | (structure) |
| 23L | (structure) |
| 23M | (structure) |

TABLE 1-continued

| No. | Compound |
|---|---|
| 23N | (structure) |
| 23O | (structure) |
| 23P | (structure) |
| 23Q | (structure) |
| 23R | (structure) |
| 23S | (structure) |
| 34A | (structure) |
| 34B | (structure) |
| 35B | (structure) |
| 35A | (structure) |
| 35C | (structure) |

Pharmaceutically acceptable salts, solvates or esters of the compounds of Table 1 are also contemplated.

In one embodiment, the compounds of formula I include compound #s 9A, 9B, 9C, 9D, 9E, and 23I.

In another embodiment, the compounds of formula I include compound #s 9A, 9C, and 9D.

In another embodiment, the compounds of formula I include compound #s 9A-F, 21C, 23A, 23I, 23R, and 23G.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. "Cycloalkyl" includes "arylcycloalkyl" and "cycloalkylaryl" as defined below. "Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Cyanoalkyl" means an alkyl as defined above wherein one or more hydrogen atoms on the alkyl is replaced by a cyano group.

"Oxo" means (=O) and "thioxo" means (=S).

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2$N-alkyl-, $Y_1Y_2$NC(O)— and $Y_1Y_2NSO_2$—, wherein $Y_1$ and $Y_2$ may be the same or different and are independently selected from the group consisting of hydrogen, alkyl, aryl, and aralkyl. "Ring system substituent" may also mean a single moiety which simultaneously replaces two available hydrogens on two adjacent carbon atoms (one H on each carbon) on a ring system. Examples of such moiety are oxy, methylene dioxy, ethylenedioxy, —C(CH$_3$)$_2$— and the like which form moieties such as, for example:

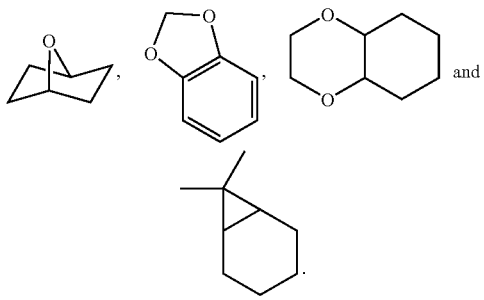

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. "Cycloalkenyl" includes "arylcycloalkenyl" and "cycloalkenylaryl" as defined below.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. "Heterocyclyl" includes "heteroarylcycloalkyl" and "cycloalkylheteroaryl" as defined below.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted by one or more ring system substituents, wherein "ring system substituent" is as defined above. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined herein by removal of hydrogen atom from the aryl portion. Non-limiting examples of suitable cycloalkenylaryls are as described herein for an arylcycloalkenyl, except that the bond to the parent moiety is through an aromatic carbon atom.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like. The bond to the parent moiety is through a non-aromatic carbon atom.

"Cycloalkylheteroaryl" means a group derived from a fused beteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkynyl" means an aryl-alkynyl- group in which the aryl and alkynyl are as previously described. Preferred aralkynyls contain a lower alkynyl group. The bond to the parent moiety is through the alkynyl. Non-limiting examples of suitable aralkynyl groups include phenacetylenyl and naphthylacetylenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkynyl" means an heteroaryl-alkynyl- group in which the heteroaryl and alkynyl are as previously described. Preferred heteroaralkynyls contain a lower alkynyl group. Non-limiting examples of suitable heteroaralkynyl groups include pyrid-3-ylacetylenyl and quinolin-3-ylacetylenyl. The bond to the parent moiety is through the alkynyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups are as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. A non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$S(O_2)$— group. The bond to the parent moiety is through the sulfonyl.

"Arylsulfinyl" means an aryl-S(O)— group. The bond to the parent moiety is through the sulfinyl.

It is noted that carbons of formula I can be replaced with 1-3 silicon atoms, provided all valency requirements are satisfied.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

When any variable (e.g., aryl, heterocycle, $R^2$, etc.) occurs more than one time in any constituent or formula, its definition on each occurrence is independent of its definition at every other occurrence.

As used herein, the term "composition" is intended to encompass a product comprising the specified ingredients in the specified amounts, as well as any product which results, directly or indirectly, from a combination of the specified ingredients in the specified amounts.

Lines drawn into the ring systems, such as, for example:

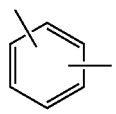

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

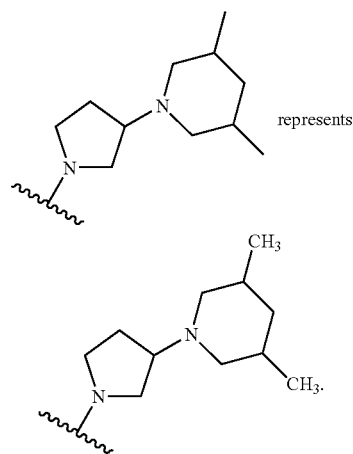

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a compound of formula I contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —P(O)$(OH)_2$, —P(O)(O$(C_1-C_6)$alkyl$)_2$ or glycosyl (the radical resulting from the removal of a hydroxyl group of the hemiacetal form of a carbohydrate), and the like.

If a compound of formula I incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

"Effective amount" or "therapeutically effective amount" is meant to describe an amount of a compound or a composition of the present invention effective in antagonizing mGluRs, in particular mGluR1, and thus producing the desired therapeutic, ameliorative, inhibitory or preventative effect in a suitable patient.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use,* (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl) ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. For example, if a compound of formula I incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formula I may be atropisomers (e.g., substituted biaryls) and are considered as part of this invention. Enantiomers can also be separated by use of chiral HPLC column.

Polymorphic forms of the compounds of formula I, and of the salts, solvates and prodrugs of the compounds of formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples herein below, by substituting an appropriate isotopically labelled reagent for a non-isotopically labelled reagent.

The compounds according to the invention have pharmacological properties; in particular, the compounds of formula I can be mGluR (metabotropic glutamate receptor) antagonists, more particularly, selective mGluR1 antagonists. Accordingly, the present compounds are useful in the treatment or prevention of conditions that are treatable or preventable by inhibiting mGluR, more particularly, mGluR1 function. Such conditions include a variety of acute and chronic neurological disorders associated with excessive or inappropriate stimulation of excitatory amino acid transmission as well as conditions which lead to glutamate-deficient functions.

Examples of treatable or preventable acute neurological disorders include, but are not limited to, cerebral deficits subsequent to cardiac bypass surgery and grafting, cerebral ischemia, stroke (ischemic or hemorrhagic), spinal cord injuries (due to trauma, infarction/ischemia or inflammation), head trauma, perinatal hypoxia, cardiac arrest and hypoglycemic neuronal damage. Examples of treatable or preventable chronic neurological disorders include, but are not limited to, Alzheimer's disease, Huntington's Chorea, amyotrophic lateral sclerosis (ALS), AIDS-induced dementia, inherited ataxias, ocular damage and retinopathy, cognitive disorders, and idiopathic and drug-induced Parkinson's. Other conditions associated with glutamate dysfunctions treatable or preventable by compounds of formula I include, but are not limited to, muscle spasms, convulsions (e.g., epilepsy), spasticity, migraine (including menstrual migraine), psychoses (e.g., schizophrenia and bipolar disorder), urinary incontinence, anxiety and related disorders (e.g. panic attack), emesis, brain edema, tardive dyskinesia, depression, drug tolerance and withdrawal (e.g., opiates, benzodiazepines, nicotine, cocaine, or ethanol), and smoking cessation.

The compounds of formula I are also useful for treating or preventing pain which may be neuropathic (nerve damage) or inflammatory (tissue damage). These compounds are particularly useful for treating or preventing neuropathic pain. Neuropathic pain used herein refers to an abnormal state of pain sensation, in which a reduction of pain threshold and the like are continued, due to functional abnormalities accompanying damage or degeneration of a nerve, plexus or perineural soft tissue, which is caused by wound, compression, infection, cancer, ischemia and the like, or metabolic disorders such as diabetes mellitus and the like. Neuropathic pain includes pain caused by either central or peripheral nerve damage. It also includes the pain caused by either mononeuropathy or polyneuropathy. In some embodiments, the neuropathic pain is induced by diabetes. In other embodiments, the neuropathic pain is induced by compression of nerves.

Examples of neuropathic pain treatable or preventable by the present compounds include, but are not limited to, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, cancer pain, central pain, labor pain, myocardial infarction pain, post-stroke pain, pancreatic pain, colic pain, muscle pain, post-operative pain, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, arthritic pain (e.g., pain due to osteoarthritis or rheumatoid arthritis), bursitis, pain associated with AIDS, visceral pain (e.g., interstitial cystitis and irritable bowel syndrome (IBS)), pain due to spinal trauma and/or degeneration, burn pain, referred pain, enhanced memory of pain and neuronal mechanisms involved in coping with pain. The compounds of the present invention are particularly useful for treating or preventing allodynia and hyperalgesia.

Compounds of formula I are also useful for treating or preventing pain associated with inflammation or an inflammatory disease in a patient. The pain associated with inflammation or an inflammatory disease treatable or preventable by the present compounds may arise where there is an inflammation of the body tissue which may be a local inflammatory response and/or a systemic inflammation. For example, the present compounds can be used to treat or prevent pain associated with inflammatory diseases including, but not limited to, organ transplant rejection; reoxygenation injury resulting from organ transplantation including transplantation of the heart, lung, liver, or kidney; chronic inflammatory diseases of the joints, including arthritis, rheumatoid arthritis, osteoarthritis and bone diseases associated with increased bone resorption; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection and necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer.

The present compounds can also be used for treating or preventing pain associated with an inflammatory disease that involves a systemic inflammation of the body, such as gram-positive or gram negative shock, hemorrhagic or anaphylactic shock, shock induced by cancer chemotherapy in response to pro-inflammatory cytokines (e.g., shock associated with pro-inflammatory cytokines), and shock induced by a chemotherapeutic agent that is administered as a treatment for cancer.

One aspect of this invention relates to a method of selectively antagonizing mGluR1 in a cell in need thereof, comprising contacting said cell with at least one compound of formula I or a pharmaceutically acceptable salt or solvate thereof.

The term "antagonist of metabotropic glutamate receptor (e.g., mGluR1)" refers to a compound that binds to the metabotropic glutamate receptor (e.g., mGluR1) but fails to elicit a response thereby blocking agonist action, i.e, inhibiting a function of mGluRs (e.g., mGluR1). Accordingly, mGluR (e.g., mGluR1) mediated processes and responses can be inhibited with an antagonist of mGluR (e.g., mGluR1). Preferably, an antagonist selectively antagonizes group I mGluRs. More preferably, an antagonist of the present invention is a selective antagonist of mGluR1. A selective antagonist of mGluR1 is one that antagonizes mGluR1, but antagonizes other mGluRs only weakly or substantially not at all, or at least antagonizes other mGluRs with an $IC_{50}$ at least 10 or even 100 or 1000 times greater than the $IC_{50}$ at which it antagonizes mGluR1. Most preferred antagonists are those which can selectively antagonize mGluR1 at low concentrations, for example, those that cause a level of antagonism of 50% or greater at a concentration of 1 OOnM or less.

Another aspect of this invention relates to a method of treating or preventing a disease or condition associated with mGluR1 in a mammal (e.g., human) in need thereof comprising administering a therapeutically effective amount of at least one compound of formula I or a pharmaceutically acceptable salt or solvate thereof to said mammal.

A preferred dosage is about 0.001 to 500 mg/kg of body weight/day of the compound of formula I. An especially preferred dosage is about 0.01 to 25 mg/kg of body weight/day of a compound of formula I or a pharmaceutically acceptable salt or solvate thereof.

The compounds of this invention may also be useful in combination (administered together or sequentially) with one or more additional therapeutic agents for the treatment of the above disorders or conditions. Such additional therapeutic agents may be a pain management agent, including non-opioid analgesics such as acetylsalicylic acid, choline magnesium trisalicylate, acetaminophen, ibuprofen, fenoprofen, diflusinal, and naproxen; and opioid analgesics, such as morphine, hydromorphone, methadone, levorphanol, fentanyl, oxycodone, and oxymorphone. Other such therapeutic agents may be a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing urinary incontinence (UI), an agent for treating Alzheimer's disease, an agent for treating or preventing inflammatory bowel disease (IBD), an agent for treating or preventing inflammatory bowel syndrome (IBS), an agent for treating Parkinson's disease and parkinsonism, an agent for treating anxiety, an agent for treating epilepsy, an agent for treating a stroke, an agent for treating psychosis, an agent for treating Huntington's chorea, an agent for treating ALS, an agent for treating vomiting, an agent for treating dyskinesia, or an agent for treating depression, and mixtures thereof.

If formulated as a fixed dose, such combination products employ the compounds of this invention within the dosage range described herein and the other pharmaceutically active agent or treatment within its dosage range. Compounds of formula I may also be administered sequentially with known therapeutic agents when a combination formulation is inappropriate. The invention is not limited in the sequence of administration; compounds of formula I may be administered either prior to or after administration of the known therapeutic agent. Such techniques are within the skills of persons skilled in the art as well as attending physicians.

Accordingly, in one aspect, this invention includes combinations comprising an amount of at least one compound of formula I or a pharmaceutically acceptable salt or solvate thereof, and an amount of one or more additional therapeutic agents listed above wherein the amounts of the compounds/treatments result in a desired therapeutic effect.

The pharmacological properties of the compounds of this invention may be confirmed by a number of pharmacological assays. The selective antagonistic activity of the present compounds towards the metabotropic glutamate receptor 1 (mGluR1) may be assayed by methods known in the art, for example, by using the methods as described in the examples.

The actions of the compounds of formula I for the treatment or prevention of pain may be assessed by various animal models, for example, by the following tests:

Formalin test: Mice are gently restrained and 30 μl of formalin solution (1.5% in saline) is injected subcutaneously into the plantar surface of the right hind paw of the mouse, using a microsyringe with a 27 gauge needle. After the formalin injection, the mouse is immediately put back into the Plexiglas observation chamber (30×20×20 cm) and the nociceptive response of the animal to formalin injection is observed for a period of 60 min. The duration of licking and flinching of the injected paw is recorded and quantified every 5 min for the total observation period. The recording of the early phase (first phase) starts immediately and lasts for 5 min. The late phase (second phase) starts about 10-15 min after formalin injection.

L5 and L6 spinal nerve ligation of the sciatic nerve (neurorpathic pain model): The peripheral neuropathy is produced by ligating the L5 and L6 spinal nerves of the right sciatic nerve, according to the method previously described by Kim and Chung (1992) except for small changes. Briefly, rats are anaesthetized with chloral hydrate (400 mg/kg, i.p.), placed in a prone position and the right paraspinal muscles separated from the spinous processes at the L4-S2 levels. The L5 transverse process is carefully removed with a small rongeur to identify the L4-L5 spinal nerves. The right L5 and L6 spinal nerves are isolated and tightly ligated with 7/0 silk thread. A complete hemostasis is confirmed and the wound sutured.

Chronic constriction injury (CCI) of the sciatic nerve (neuropathic pain model): Surgery is performed according to the method described by Bennett & Xie (1987). Rats are anaesthetized with chloral hydrate (400 mg/kg, i.p.) and the common sciatic nerve is exposed at the level of the mid-thigh. Proximally, at about 1 cm from the nerve trifurcation, four loose ligatures (4/0 silk) spaced 1 mm are tied around the nerve. The ligature delays, but does not arrest, circulation through the superficial epineural vasculature. The same procedure is performed except for ligature placement (sham surgery) in a second group of animals.

Carrageenan (inflammatory pain model): The right hind paw of each animal is injected at subplantar level with 0.1 mL of carrageenan (25 GA needle). Pre-tests are determined prior to carrageenan or drug administration. In POST-TREATMENT protocol, rats are tested 3 hours after carrageenan treatment to establish the presence of hyperalgesia and then at different times after drug administration. In PRE-TREATMENT protocol, one hour after drug administration, rats are treated with carrageenan and they are tested starting from 3 hours later.

Freund's adjuvant-induced arthritic model (inflammatory pain model): Animals receive a single subplantar injection of 100 mL of a 500 mg dose of heat-killed and dried *Mycobacterium tuberculosis* (H37 Ra, Difco Laboratories, Detroit, Mich., USA) in a mixture of paraffin oil and an emulsifying agent, mannide monooleate (complete Freund's adjuvant). Control animals are injected with 0.1 mL mineral oil (incomplete Freund's adjuvant).

Measurement of tactile allodynia (behavioural test): Behavioral tests are conducted by observer blinded to the treatment during the light cycle to avoid circadian rhythm fluctuation. Tactile sensitivity is evaluated using a series of calibrated Semmes-Weinstein (Stoelting, Ill.) von Frey filaments, bending force ranging from 0.25 to 15 g. Rats are placed in a transparent plastic box endowed with a metal mesh floor and are habituated to this environment before experiment initiation. The von Frey filaments are applied perpendicularly to the midplantar surface of the ipsilateral hind paws and the mechanical allodynia is determined by sequentially increasing and decreasing the stimulus strength ("up-down" paradigm of the filament presentation). Data are analysed with a Dixon non-parametric test (Chaplan et al. 1994). Paw licking or vigorously shaking after stimulation is considered pain-like responses.

Thermal hyperalgesia (behavioural test): Thermal hyperalgesia to radiant heat is assessed by measuring the withdrawal latency as an index of thermal nociception (Hargreaves et al., 1998). The plantar test (Basile, Comerio, Italy) is chosen because of its sensitivity to hyperalgesia. Briefly, the test consists of a movable infrared source placed below a glass plane onto which the rat is placed. Three individual perspex boxes allow three rats to be tested simultaneously. The infrared source is placed directly below the plantar surface of the hind paw and the paw withdrawal latency (PWL) is defined as the time taken by the rat to remove its hind paw from the heat source. PWLs are taken three times for both hind paws of each rat and the mean value for each paw represented the thermal pain threshold of rat. The radiant heat source is adjusted to result in baseline latencies of 10-12 sec. The instrument cut-off is fixed at 21 sec to prevent tissue damage.

Weight bearing (behavioural test): An incapacitance tester is employed for determination of hind paw weight distribution. Rats are placed in an angled plexiglass chamber positioned so that each hind paw rested on a separate force plate. The weight bearing test represents a direct measure of the pathological condition of the arthritic rats without applying any stress or stimulus, thus this test measures a spontaneous pain behaviour of the animals.

While it is possible for the active ingredient to be administered alone, it is preferable to present it as a pharmaceutical composition. The compositions of the present invention comprise at least one active ingredient, as defined above, together with one or more acceptable carriers, adjuvants or vehicles thereof and optionally other therapeutic agents. Each carrier, adjuvant or vehicle must be acceptable in the sense of being compatible with the other ingredients of the composition and not injurious to the mammal in need of treatment.

Accordingly, this invention also relates to pharmaceutical compositions comprising at least one compound of formula I, or a pharmaceutically acceptable salt, solvate or ester thereof and at least one pharmaceutically acceptable carrier, adjuvant or vehicle.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts, solvates or esters thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of formula I or a pharmaceutically acceptable salt, solvate, or ester thereof and at least one pharmaceutically acceptable carrier, adjuvant or vehicle.

Yet another aspect of this invention is a kit comprising an amount of at least one compound of formula I or a pharmaceutically acceptable salt, solvate or ester thereof and an amount of at least one additional therapeutic agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz), Varian Mercury VX400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me = methyl; Et = ethyl; Pr = propyl; Bu = butyl; Ph = phenyl, and Ac = acetyl
μl = microliters
AcOEt or EtOAc = ethyl acetate
AcOH or HOAc = acetic acid
ACN = acetonitrile
atm = atmosphere
Boc or BOC = tert-butoxycarbonyl
DCM or $CH_2Cl_2$: dichloromethane:
DIPEA = diisopropylethylamine
DMAP = 4-dimethylaminopyridine
DMF = dimethylformamide
DMS = dimethylsulfide
DMSO = dimethyl sulfoxide
EDCI = 1-(3-dimethylaminopropyl)-3-ethylcarbodiimide
Fmoc = 9-fluorenylmethoxycarbonyl
g = grams
h = hour
HATU = O-(7-azabenzotriazol-1-yl)-N,N,N',N'-tetramethyluronium hexafluorophosphate
HOBt = 1-hydroxybenzotriazole
LAH = lithium aluminum hydride
LCMS = liquid chromatography mass spectrometry
min = minute
mg = milligrams
mL = milliliters
mmol = millimoles
MCPBA = 3-chloroperoxybenzoic acid
MeOH: methanol
MS = mass spectrometry
NMR = nuclear magnetic resonance spectroscopy
RT or rt = room temperature (ambient, about 25° C.).
TEA or $Et_3N$ = triethylamine
TFA = trifluoroacetic acid
THF = tetrahydrofuran
TLC = thin layer chromatography
TMS = trimethylsilyl
Tos or tosyl = p-toluenesulfonyl
Tr = triphenylmethyl

EXAMPLES

In general, the compounds of this invention may be prepared from known or readily prepared starting materials, following methods known to one skilled in the art and those illustrated below. All stereoisomers and tautomeric forms of the compounds are contemplated.

Scheme 1
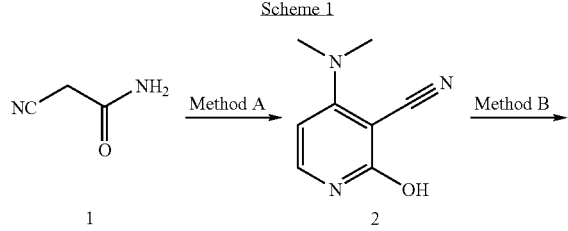
1 → Method A → 2
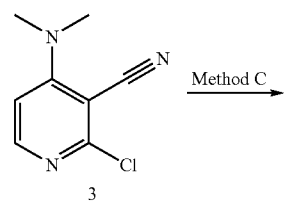
3 → Method C →
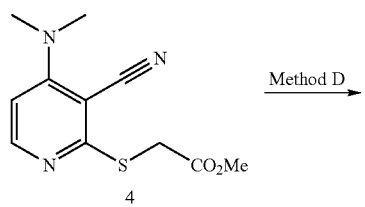
4 → Method D →
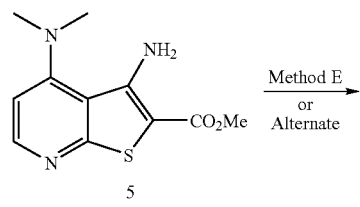
5 → Method E or Alternate →
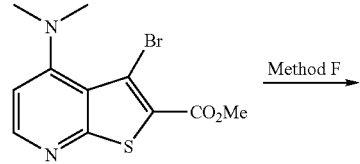
6A R = Br
6B R = I
→ Method F →
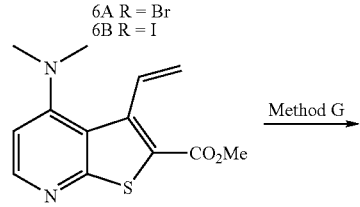
7 → Method G →
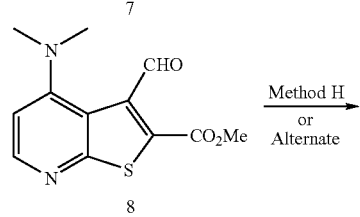
8 → Method H or Alternate →
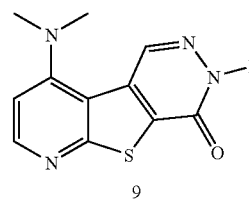
9
Scheme 2
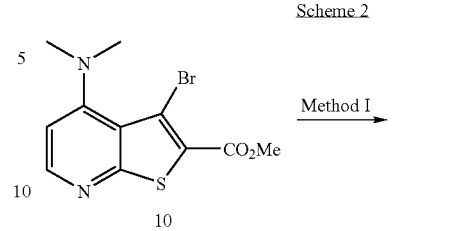
10 → Method I →
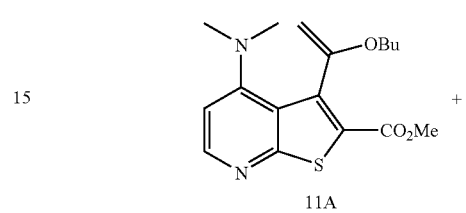
11A +
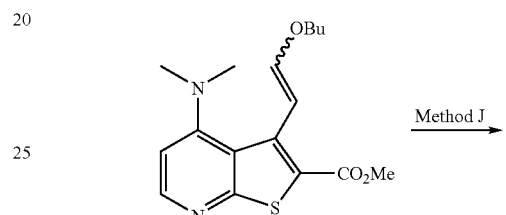
11B → Method J →
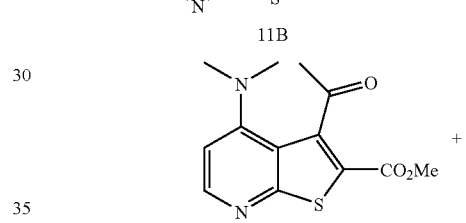
12A +
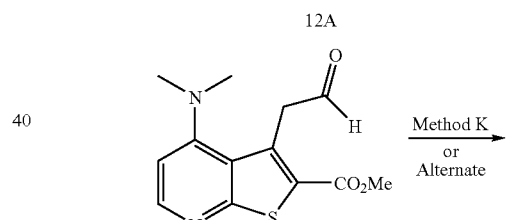
12B → Method K or Alternate →
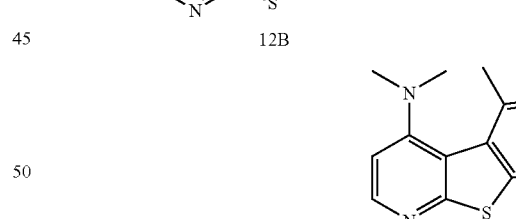
13
Scheme 3
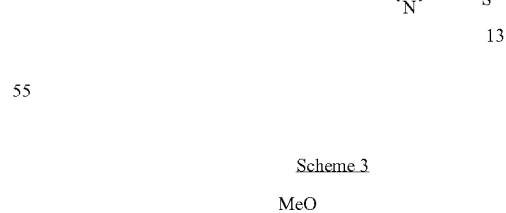
14 → Method L →
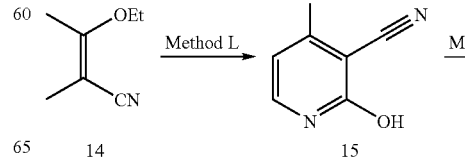
15 → Method M →

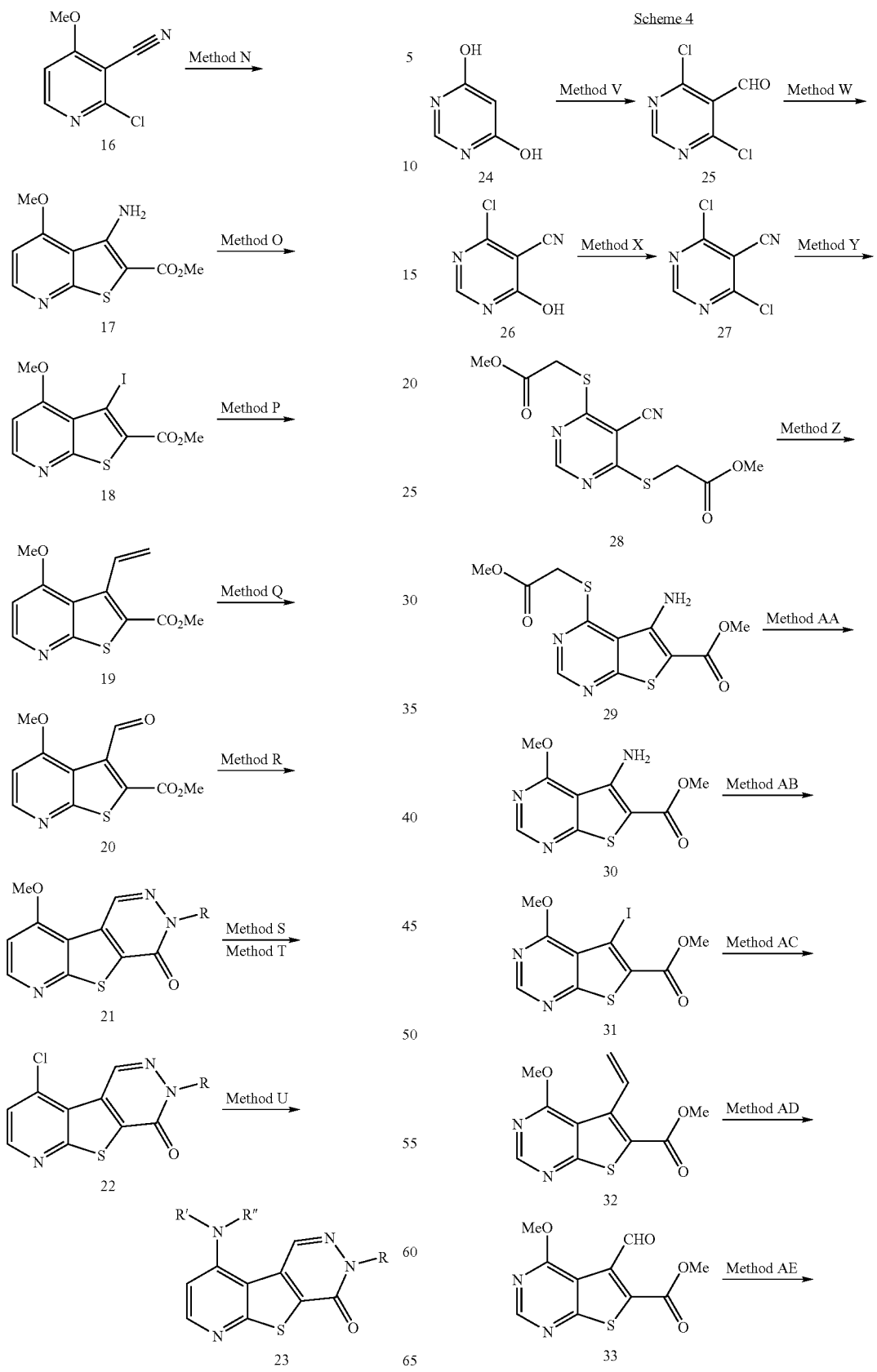

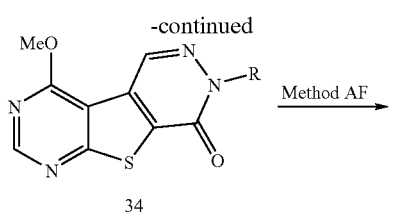

Method AF →

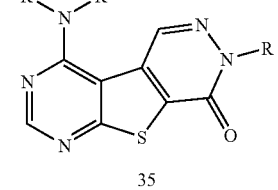

35

Experimental Procedures

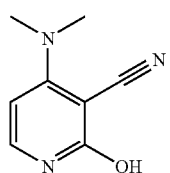

2

Method A: (Ref: H. Zipse and L.-H. Wang, *Liebigs Ann.* 1996, 1501-1509.)

A mixture of cyanoacetamide (8.4 g, 0.10 mol) and dimethylacetamide dimethylacetal (14.6 mL, 0.1 mol) was heated under reflux in dry ethanol (150 mL) for 2.5 hours under a nitrogen atmosphere. The resulting white crystals of 2-cyano-3-(dimethylamino)-2-butenamide (10.0 g, 0.07 mol) were filtered, washed with ethanol and dried under vacuum. To this was added N,N-dimethyl-formamide dimethylacetal (8.1 g, 0.07 mol) and the mixture heated under reflux in dry toluene (100 mL) for 1 hour before evaporating the solvent under reduced pressure. The residue was heated neat at 150° C. for 30 minutes, cooled, washed twice with acetone and dried under vacuum to give compound 2. $^1$H NMR (DMSO-d6) δ 7.22 (d, 1H), 5.86 (d, 1H), 3.13 (s, 6H); Mass Spectrum (M$^{+1}$): m/z calcd. for $C_8H_{10}N_3^+$=164.1, observed m/z=164.2.

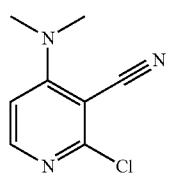

3

Method B: (Ref.: M. Yu. Yakovlev, O. B. Romanova, S. I. Grizik, A. V. Kadushkin, and V. G. Granik, *Khimiko-Farmat-sevticheskii Zhurnal*, 1997, 31(11), 44-47.)

To compound 2 (9.34 g, 0.06 mol) was added phosphorous oxychloride (95 mL, 1.02 mol) and to the mixture was added triethylamine (4 ml, 0.029 mol) dropwise. The resultant mixture was heated at reflux for a period of 3 hours, cooled to room temperature and quenched with ice-water. The mixture was then basified using 40% sodium hydroxide solution and the resulting precipitate filtered, washed with water until neutral and dried in a vacuum oven to give chloropyridine compound 3. $^1$H NMR (CDCl3): δ 7.95 (d, 1H), 6.48 (d, 1H), 3.20 (s, 6H).

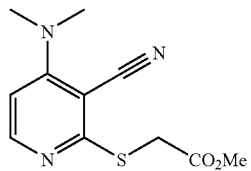

4

Method C: (Ref.: M. Yu. Yakovlev, O. B. Romanova, S. I. Grizik, A. V. Kadushkin, and V. G. Granik, *Khimiko-Farmat-sevticheskii Zhurnal*, 1997, 31(11), 44-47.)

A solution of compound 3 (6.02 g, 0.033 mol), methyl thioglycolate (7.05 g, 0.066 mol) and potassium carbonate (6.88 g, 0.050 mol) in DMF (50 mL) was stirred for a period of 5 hours at room temperature under a nitrogen atmosphere. Water (200 mL) was added, and the resulting precipitate filtered and dried in a vacuum oven to give ester 4. $^1$H NMR (CDCl3): δ 7.97 (d, 1H), 6.28 (d, 1H), 3.93 (s, 2H), 3.70 (s, 3H), 3.18 (s, 6H).

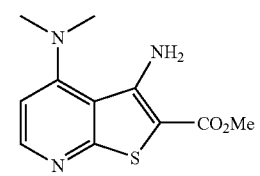

5

Method D:

A solution of compound 4 (8.33 g, 0.033 mol) and sodium methoxide (3.77 g, 0.07 mol) in methanol was heated at reflux for 3 hours under a nitrogen atmosphere. The reaction was cooled to room temperature, water was added and the product isolated by extraction with dichloromethane (150 mL). The organic layer was dried over anhydrous sodium sulfate, filtered and evaporated under reduced pressure to give the desired product 5. $^1$H NMR (CDCl3): δ 8.41 (d, 1H), 6.81 (d, 1H), 6.70 (br.s, 2H), 3.82 (s, 3H), 2.81 (s, 6H). Mass Spectrum (M$^{+1}$): m/z calcd. for $C_{11}H_{14}N_3O_2S^+$=252.1, observed m/z=252.1.

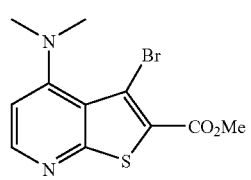

6

Method E: (Ref. Clive, D. L. J.; Sannigrahi, M.; Hisaindee; S. *J. Org. Chem.* 2001, 66, 954-961.)

A 3-neck, 2 L round bottom flask was fitted with an overhead mechanical stirrer and an addition funnel, and then charged with CuBr (4.05 g, 28.2 mmol) and aq. 48% HBr (280 mL). The resulting solution was cooled in an ice water bath and then compound 5 was added. To this cooled mixture was added a solution of NaNO$_2$ (2.44 g, 35.4 mmol) in water (65 mL), dropwise. After being stirred for 7 hours while cooled in an ice water bath, a solution of Na$_2$S$_2$O$_3$ (50 g) in water (300 mL) was added. The reaction mixture was carefully quenched by the addition of NaHCO$_3$ (solid, added in portions). Small portions of ethyl acetate were periodically added to control the foaming that occurred during the quench. The quenched mixture was poured into a separatory funnel and extracted with ethyl acetate (3×250 mL). The combined organic and emulsion layers were dried over Na$_2$SO$_3$, overnight. The dried organic layers were filtered, absorbed onto silica gel (25 g), and purified by silica gel chromatography with hexanes/ethyl acetate to afford compound 6 (3.49 g, 39%) as a yellow solid. $^1$HNMR (CDCl$_3$, 400 MHz) δ 8.37 (d, 1H), 6.77 (d, 1H), 3.90 (s, 3H), 2.93 (s, 6H); MS (M$^{+1}$): m/z calcd for C$_{11}$H$_{12}$N$_2$O$_2$SBr$^+$=314.98, 316.98, found m/z=315.07, 317.04.

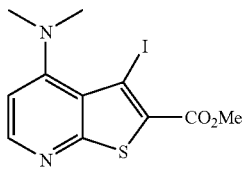

6A

Method E (Alternate):

To a 50° C. solution of Iodine (28.7 g, 113 mmol) and tert-butyl nitrite (7.8 mL, 56.7 mmol) in CH$_3$CN (250 mL) was added substrate 5 (9 g, 37.8 mmol). Vigorous stirring of the resulting suspension was continued for 1 hour. The reaction mixture was cool to room temperature and then poured into a solution of sodium bisulfite (200 g) in water (500 mL). Stirring was continued for 30 minutes, and the precipitate isolated by vacuum filtration through paper and washed with water. The solid was air dried and then put under vacuum overnight giving 6A (4.5 g) as an orange powder. $^1$HNMR (CDCl$_3$, 400 MHz) δ 8.43 (d, 1H), 6.87 (d, 1H), 3.96 (s, 3H), 2.96 (s, 6H).

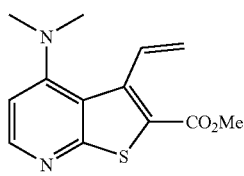

7

Method F:

A round bottom flask was charged with 6 (0.30 g, 1.14 mmol), vinyl-tri-n-butylstannane (0.37 g, 1.16 mmol) and DMF (6 mL). Nitrogen was bubbled through this mixture for several minutes with stirring. Tetrakis(triphenyl-phosphine) palladium (0.01 g, 0.08 mmol) was added to the mixture, and stirring was continued under a nitrogen atmosphere. This mixture was heated in an oil bath overnight at 70° C. To the resulting black mixture was added aq. 1 M K$_2$CO$_3$, ethyl acetate and solid KF. This mixture was stirred vigorously for 1 hour, and then the layers were separated. The aqueous layer was extracted with ethyl acetate. The combined organic layers were washed with brine dried over anhydrous sodium sulfate, filtered and purified by silica gel chromatography with hexanes/ethyl acetate to afford compound 7 (0.18 g, 70%). $^1$HNMR (CDCl$_3$, 400 MHz) δ 8.38 (d, 1H), 7.48 (dd, 1H), 6.87 (d, 1H), 5.58 (d, 1H), 5.42 (d, 1H), 3.90 (s, 3H), 2.82 (s, 6H).

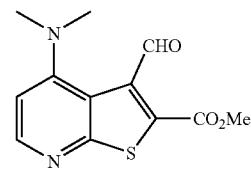

8

Method G:

Compound 7 (1.5 g, 5.7 mmol) in THF:H$_2$O (200 mL (1:1) and NaIO$_4$ (3.0 g, 14.3 mmol) was stirred at room temperature and then OsO$_4$ (6 mL, 0.07 mmol (2.5% w/w in tBuOH) was added. The reaction mixture was stirred at room temperature over the weekend. When the reaction was judged complete, 10% sodium thiosulfate was added, and the solution poured into a seperatory funnel containing ethyl acetate (300 mL) and water (300 mL). The layers separated and the aqueous layer was extracted with ethyl acetate (2×200 mL). The combined organics were dried over Na$_2$SO$_3$, filtered and concentrated to give the crude product which was subsequently purified by chromatography on silica gel eluting with ethyl acetate/hexanes mixtures to give pure aldehyde 8 (250 mg). $^1$H NMR (CDCl$_3$, 400 MHz) δ 10.79 (s, 1H), 8.37 (d, 1H), 6.76 (d, 1H), 3.98 (s, 3H), 2.90 (s, 6H).

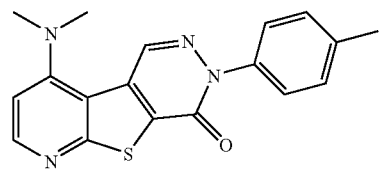

9A

Method H:

To the aldehyde 8 (25 mg 0.94 mmol) in toluene (4 mL) was added the p-tolylhydrazine hydrochloride salt and several drops of acetic acid. After heating at 75° C. overnight the reaction mixture was cooled to room temperature and treated with dimethylaminoethylamine on polystyrene resin to quench the acetic acid. The resin was removed by filtration and the residue was concentrated to give the crude product 9A, which was purified by chromatography on silica gel eluting with ethyl acetate hexanes mixtures. $^1$H NMR (CDCl$_3$, 400 MHz) δ 8.73 (s, 1H), 8.56 (d, 1H) 7.59 (d, 2H), 7.31 (d, 2H), 3.03 (s 6H) 2.42 (s, 3H). Mass Spectrum (M$^{+1}$): m/z calcd for C$_{18}$H$_{16}$N$_4$OS$^+$=337.1, observed m/z=337.2.

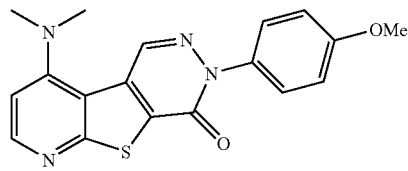

9B

Method H (Alternate):

To a solution of the aldehyde 8 (0.10 g, 0.38 mmol) in methanol (4 mL) was added the p-methoxyphenylhydrazine hydrochloride (0.20 g, 1.14 mmol) followed by concentrated aq. HCl (0.1 mL, 12 mmol). The reaction was stirred for 48 hours at 70° C. then cooled, concentrated partially, diluted with CHCl$_3$ and shaken with aqueous NaHCO$_3$. The organic layer was separated and concentrated to give the crude product which was purified by chromatography on silica gel eluting with ethyl acetate hexanes mixtures. $^1$H NMR (CDCl$_3$) δ 8.73 (s, 1H) 8.57 (d, 1H), 7.64 (d, 2H), 7.03 (d, 2H), 7.00 (s, 1H), 3.88 (s, 6H) 3.04 (s, 6H); Mass Spectrum (M$^{+1}$): m/z calcd. for C$_{18}$H$_{16}$N$_4$O$_2$S$^+$=353.1, observed 353.2.

The following compounds were made analogously.

TABLE 2

| No. | Compound | Molecular Formula | Calculated Mass | Observed Mass |
|---|---|---|---|---|
| 9A | | C$_{18}$H$_{16}$N$_4$OS | 336.10 | 337.2 |
| 9B | | C$_{18}$H$_{16}$N$_4$O$_2$S | 352.10 | 353.2 |
| 9C | | C$_{17}$H$_{13}$ClN$_4$OS | 356.05 | 357.2 |
| 9D | | C$_{17}$H$_{13}$BrN$_4$OS | 400.00 | 401.2 |
| 9E | | C$_{18}$H$_{13}$N$_5$OS$_2$ | 379.06 | 380.02 |
| 9F | | C$_{18}$H$_{13}$N$_5$OS$_2$ | 379.06 | 380.02 |

TABLE 2-continued

| No. | Compound | Molecular Formula | Calculated Mass | Observed Mass |
|---|---|---|---|---|
| 9G | | $C_{17}H_{20}N_4OS$ | 328.14 | 329.2 |

11A

11B

Method I:

A reaction vial was charged with compound 10 (0.71 g, 2.26 mmol), n-butyl vinyl ether (1.5 mL, 11.5 mmol), sodium acetate (1.0 g, 12 mmol), palladium (II) acetate (0.076 g, 0.34 mmol), and N-methylpyrrolidinone (7 mL), sealed, and then placed in a 90° C. oil bath. After being heated and stirred in the oil bath for 4.25 hours, the reaction mixture was diluted with ethyl acetate (100 mL) and washed with water (2×100 mL). The resulting organic layer was dried over $Na_2SO_4$, filtered, absorbed onto silica gel (7 g), and purified by silica gel chromatography with hexanes/ethyl acetate to afford a mixture of compound 11A and 11B (E-11B:Z-11B, 1.5:1) as a 3:2 mixture, respectively (0.505 g, 67%). $^1$HNMR (CDCl$_3$, 400 MHz) δ 8.32-8.31 (m, 1H from 11A, Z-isomer of 11B, and E-isomer of 11B), 6.90 (d, 1H, E-isomer of 11B), 6.85 (d, 1H, E-isomer of 11B), 6.72-6.66 (m, 1H from A, Z-isomer of 11B, and E-isomer of 11B), 6.26 (d, 1H, Z-isomer of 11B), 6.00 (d, 1H, Z-isomer of 11B), 4.46 (s, 1H, 1A), 4.13 (s, 1H, 11A), 3.93-3.70 (m, 2H from 11A and one isomer of 11B), 3.72 (t, 2H, one isomer of 11B), 2.89 (s, 3H from 11A, Z-isomer of 11B, and E-isomer of 11B), 2.86 (s, 3H from 11A, Z-isomer of 11B, and E-isomer of 11B), 1.75-1.20 (m, 6H from 11A, Z-isomer of 11B, and E-isomer of 11B), 0.99-0.93 (t, 3H, one isomer of 11B), 0.82 (t, 3H, one isomer of 11B); Mass Spectrum $(M^{+1})$ m/z calcd. for $C_{17}H_{23}N_2O_3$ $S^+$=335.14, observed m/z=335.15.

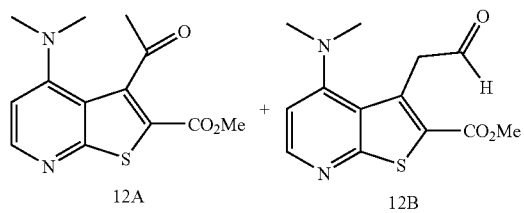

12A  12B

Method J:

Aq. 1 M HCl (2.6 mL) was added to a solution of compounds 11A and 11B (0.43 g, 1.29 mmol) in tetrahydrofuran (9 mL). This solution was then heated at reflux for 3 hours. The reaction solution was then diluted with dichloromethane (10 mL) and poured into saturated aq. NaHCO$_3$ (100 mL). This mixture was stirred vigorously for 10 minutes, and then the layers were separated. The aq. layer was extracted with dichloromethane (2×10 mL). The combined organic layers were dried over $Na_2SO_4$, filtered, absorbed onto silica gel (4 g), and purified by silica gel chromatography with hexanes/ethyl acetate to afford compound 12A (0.189 g, 53%) as a yellow solid, along with compound 12B (0.064 g, 18%) as a yellow solid. Data for compound 12A: $^1$HNMR (CDCl$_3$, 400 MHz) δ 8.47 (d, 1H), 6.89 (d, 1H), 3.86 (s, 3H), 2.70 (s, 6H), 2.50 (s, 3H); MS $(M+1)^+$ m/z calcd for $C_{13}H_{15}N_2O_3$ $S^+$=279.08, found m/z=279.12. Data for compound 12B: $^1$HNMR (CDCl$_3$, 400 MHz) δ 9.62 (s, 1H), 8.45 (d, 1H), 6.87 (d, 1H), 5.25 (s, 1H), 4.58 (s, 2H), 3.87 (s, 3H), 2.72 (s, 6H); Mass Spectrum $(M^{+1})$: m/z calcd. for $C_{13}H_{15}N_2O_3$ $S^+$=279.08, observed m/z=279.07.

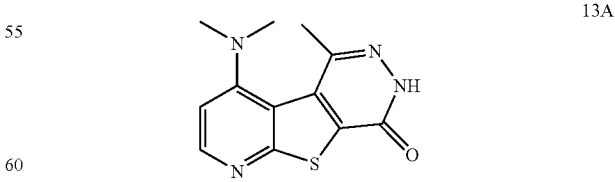

13A

Method K:

A reaction vessel was charged with compound 12A (0.014 g, 0.050 mmol), hydrazine monohydrate (0.024 mL, 0.49 mmol), and ethanol (0.5 mL), sealed, and placed in a 110° C. oil bath. After being heated for 17.5 hours, the reaction mixture was cooled and dissolved in dichloromethane/methanol. This solution was then shaken with PS-Benzaldehyde resin (1.50 mmol/g) for 1.5 hours. The resulting mixture was filtered, and the isolated filtrate was concentrated to afford compound 13A (0.0139 g, quantitative yield). $^1$HNMR (CDCL$_3$, 500 MHz) δ 8.51 (d, 1H), 7.20 (d, 1H), 2.96 (s, 6H), 2.71 (s, 3H); Mass Spectrum (M$^{+1}$): m/z calcd. for m/z calcd for $C_{12}H_{13}N_4OS^+$=261.1, observed m/z=261.0.

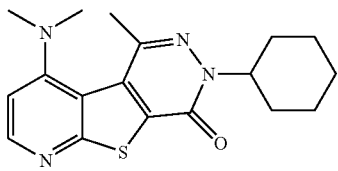

13C

Method K (Alternate):

A reaction vessel was charged with compound 12A (0.044 g, 0.158 mmol), cyclohexylhydrazine hydrochloride (0.048 g, 0.32 mmol), triethylamine (0.044 mL, 0.32 mmol), and ethanol (1.6 mL), sealed, and placed in an 80° C. oil bath. After being heated for 2.5 days, additional cyclohexylhydrazine hydrochloride (0.24 g, 1.6 mmol) and triethylamine (0.33 mL, 2.4 mmol) were added to the reaction mixture. After being heated for 1 day, the reaction solution was cooled, diluted with dichloromethane, and shaken with PS-Benzaldehyde resin (1.50 mmol/g) for 2 hours. The resulting mixture was filtered, and then the filtrate was absorbed onto silica gel (5 g) and purified by silica gel chromatography with methanol/aqueous ammonium hydroxide/dichloromethane to afford compound 13B along with minor impurities. Impure compound 13B was purified by silica gel chromatography with methanol/aqueous ammonium hydroxide and dichloromethane to afford compound 13B (0.0125 g, 23%) as a white solid. $^1$HNMR (CDCl$_3$, 400 MHz) δ 8.39 (d, 1H), 6.86 (d, 1H), 4.96 (m, 1H), 2.84 (s, 6H), 2.66 (s, 3H), 1.86-1.18 (m, 10H); Mass Spectrum (M$^{+1}$): m/z calcd. for $C_{18}H_{23}N_4OS^+$=343.2, observed m/z=343.1.

The following compounds were prepared analogously.

| No. | Compound | Molecular Formula | Calculated Mass | Observed Mass |
|---|---|---|---|---|
| 13A | | C12H12N4OS | 260.07 | 261.0 |
| 13B | | C19H18N4OS | 350.12 | 351.1 |
| 13C | | C18H22N4OS | 342.15 | 343.1 |
| 13D | | C18H16N4O2S | 352.10 | 353.2 |

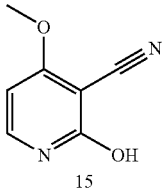

15

Method L: (Refs: (a) S. Yano, T. Ohno, K. Ogawa, *Heterocycles* 1993, 36, 145. (b) M. Mittelbach, G. Kastner, H. Junek, *Arch. Pharm.* 1985, 318, 481.)

(1-Ethoxyethylidene)malononitrile (14) (40.0 g, 294 mmol) and N,N-dimethylformamide dimethyl acetal (63.0 ml, 470 mmol) were reacted according to Mittelbach and Yano's procedures to give 23.5 g of 15 as a yellow-orange solid. $^1$H NMR (DMSO-$d_6$, 400 MHz) δ 12.12 (bs, 1H), 7.77 (d, 1H), 6.33 (d, 1H), 3.95 (s, 3H).

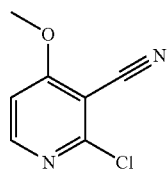

16

Method M:

To compound 15 (23.5 g, 157 mmol) was added POCl$_3$ (300 mL) and Et$_3$N (15 mL). The reaction mixture was stirred at reflux for 2 hours and the solvents removed in vacuo. The resulting brown solid was quenched drop wise with water and basified with 40% aq. NaOH. The aqueous suspension was extracted with three 100 mL portions of dichloromethane, dried over MgSO$_4$ and concentrated in vacuo to provide 23.9 g of compound 16 as a brown solid. $^1$H NMR (CDCl$_3$, 400 MHz) δ 8.42 (d, 1H), 6.89 (d, 1H), 4.03 (s, 3H).

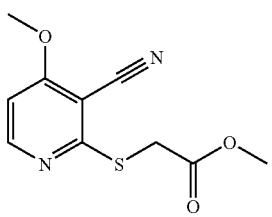

17

Method N:

To a solution of compound 16 (10.0 g, 59.2 mmol) in 200 mL of DMF was added methylthioglycolate (7.15 mL, 65.0 mmol) and sodium methoxide (3.60 g, 65.0 mmol). The reaction was allowed to stir at room temperature for 2 h and poured onto 500 mL of water. The solid was filtered off and recrystallized from ethanol to give 10.0 g of compound 17 as a yellow solid. $^1$H NMR (CDCl3) δ 8.37 (d, 1H), 6.64 (d, 1H), 4.02 (s, 2H), 3.97 (s, 3H), 3.74 (s, 3H).

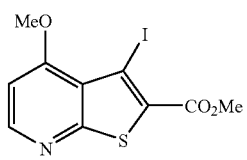

18

Method O:

To a 48° C. solution of Iodine (80 g, 315 mmol) and tert-butyl nitrite (16 mL, 157 mmol) in CH$_3$CN (1 L), was added substrate 17 (25 g, 105 mmol). Vigorous stirring of the resultant suspension was continued for 1 hour, at which time the reaction was judged complete by MS. The reaction mixture was cool to room temperature and then poured into a solution of sodium bisulfite (500 g) in water (2.5 L). Stiring was continued for 30 minutes and then the precipitate isolated by vacuum filtration through paper. The tan solid air dried in the air and then put under vacuum overnight giving 18 (20 g) as an off white powder. $^1$H NMR (400 MHz:CDCl$_3$) δ8.54 (d, 1H), 6.74 (d, 1H), 3.99 (s, 3H), 3.92 (s, 3H).

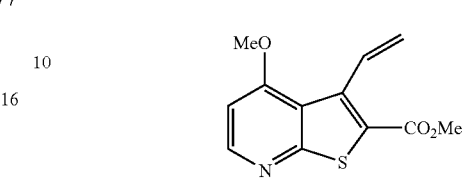

19

Method P:

The Iodide 18 (40 g, 30.9 mmol) and tri-n-butylallylstannane (9 mL, 31.4 mmol) were added to DMF (100 mL) at room temperature and a stream of N$_2$ was bubbled through the solution for 5 minutes. Pd(PPh$_3$)$_4$ (800 mg, 0.7 mmol) was added and the reaction mixture heated to 85° C. for 48 hours. The reaction mixture was returned to room temperature, transferred to a seperatory funnel containing ethyl acetate (500 mL) and water (500 mL), and vigorously shaken. The organic layer was removed and the aqueous layer extracted two additional times 100 mL each. $^1$H NMR (CDCl$_3$, 400 MHz): δ 8.52 (br. s, 1H), 7.24 (dd, 1H), 6.75 (br. s, 1H), 5.61 (m, 2H), 3.98 (s, 3H), 3.89 (s, 3H).

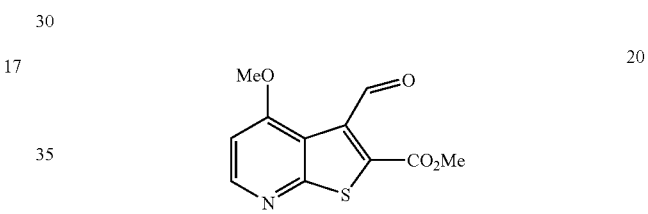

20

Method Q:

To a solution of 19 (2.2 g, 8.8 mmol) in THF:$^t$BuOH:H$_2$O (300 mL:150 mL:300 mL) was added sodium periodate (4 g, 18 mmol) followed by OSO$_4$ (4 mL, 0.39 mmol, 2.5% v/v solution in $^t$BuOH). The reaction mixture was stirred at room temperature, precipitate formation was noticed at about 20 minutes, and stirring continued overnight. The reaction was quenched with sodium thiosulphate (20% aq.) and then diluted with ethyl acetate. The aqueous layer was further extracted with ethyl acetate (3×) followed by chloroform (1×). The combined organics were dried and concentrated to give a dark red tar which was dissolved in chloroform and triturated with ether. Filtration and drying provided 20 (2.2 g). $^1$H NMR (CDCl$_3$, 400 MHz) δ 10.62 (s, 1H), 8.57 (d, 1H), 6.81 (d, 1H), 4.01 (s, 3H), 3.96 (s, 3H).

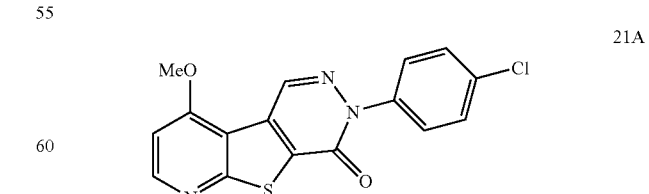

21A

Method R:

The aldehyde 20 (2.2 g, 8.8 mmol) in methanol/CH$_2$Cl$_2$ (100 mL 3/1), was treated with p-chlorohydrazine hydrochloride (1.8 g, 10.1 mmol) and concentrated aq. HCl (0.5 mL). The reaction was heated at 45° C. overnight. The reaction mixture was diluted with CHCl₃ and then washed with sodium bicarbonate. The aqueous layer was extracted with CHCl₃ (2×), the organics dried over sodium sulfate and concentrated to dryness. The residue was purified by trituration with chloroform and methanol to provide the product 21A as a grey solid. ¹H NMR (400 MHz:CDCl₃) δ 8.78 (s, 1H) 8.55 (br. s, 1H), 7.55 (d, 2H), 7.19 (d,2H), 6.92 (s, 1H), 4.05 (s, 3H). Mass Spectrum (M⁺¹): m/z calcd. for $C_{16}H_{10}ClN_3O_2S$=343.02, observed m/z=344.2.

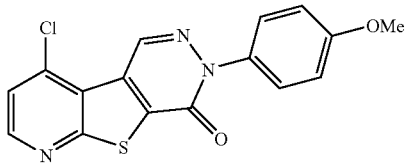
22B

| No. | Compound | Molecular Formula | Calculated Mass | Observed Mass |
|---|---|---|---|---|
| 21A | | $C_{16}H_{10}ClN_3O_2S$ | 343.02 | 344.2 |
| 21B | | $C_{17}H_{13}N_3O_3S$ | 339.07 | 340.2 |
| 21C | | $C_{17}H_{13}N_3O_2S$ | 323.07 | 324.2 |

22A

Method S, Step 1:

Compound 21A (610 mg) was treated with 20 mL of HBr (33% in acetic acid), and heated at 100° C. for 4 hours. The suspension was cooled to room temperature, and the solid material isolated by filtration and washed with water. The material was dried by co-evaporation with acetonitrile and then CHCl₃ to give a grey/brown solid, which was used without further purification; see Method S, Step 2 below.

Method S, Step 2:

The crude material from Step 1 was treated with POCl₃ (10 mL) and triethylamine (2 mL) and heated to 60° C. for 2 hours. The reaction mixture was partially concentrated and poured over ice, the pH adjusted to 7-8 with aq. NaOH and extracted with ethiyl acetate (3×). The combined organics were washed with brine, dried over sodium sulfate and concentrated. The crude residue was purified by chromatography on silca gel eluting with dichloromethane/acetone mixtures to give 22A. ¹H NMR (CDCl₃, 400 MHz): δ 9.14 (s, 1H), 8.68 (s, 1H), 7.67 (d, 2H), 7.54 (d, 1H), 7.45 (d, 2H).

Method T:

Step 1; Solid 21B (500 mg, 0.58 mmol) and pyridine hydrochloride (2.0 g, 115 mmol) were heated with a heat gun until a homogenous liquid was formed and then left to cool and solidify at room temperature. To the solid mixture was added 3N HCl (100 mL). The solid was broken up and stirred for 30 minutes and filtered. The filter cake was washed with water until the filtrate became neutral. The solid was dissolved in chloroform and acetonitrile and evaporated to dryness. The yellow solid was used without further purification.

Step 2; The residue was taken up in CH₂Cl₂ and treated with triethylamine (1 mL) and POCl₃ (3 mL) and stirred overnight at room temperature. The reaction mixture was diluted with chloroform and poured over ice, the pH adjusted to 8 with NaHCO₃ (sat. aq.) and the layers separated. The aqueous was extracted with chloroform (2×30 mL), the organics dried with sodium sulfate and concentrated. The residue was chromatographed on silica gel, eluting with hexanes/acetone mixtures. The product-containing fractions were concentrated to give the product 22B (150 mg). ¹H NMR (CDCl3, 400 MHz) δ 9.16 (s, 1H), 8.71 (d, 1H), 7.64 (d, 2H), 7.57 (d, 1H), 7.03 (s, 2H), 3.88 (s, 3H).

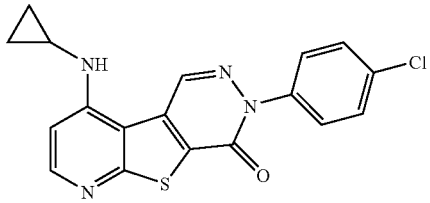

23A

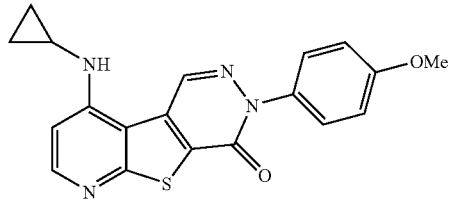

23B

Method U:

A mixture of chloride 22B (50 mg, 0.15 mmol) and cyclopropylamine (200 mL) in dioxane (4 mL) were heated in a sealed vial for 18 hours. The reaction mixture was diluted with chloroform, shaken with sodium bicarbonate and the organic layer separated from the aqueous by filtration through a SPE cartridge fitted with a hydrophobic frit. The solvent was removed and the residue chromatographed on silica gel eluting with hexanes/acetone mixtures to give 23A. $^1$H NMR (CDCl$_3$, 400 MHz): δ 8.42 (br. s, 2H), 7.62 (d, 2H), 7.40 (d, 2H), 7.05 (d, 1H), 5.39 (br. s, 1H) 2.65 (m, 1H), 0.98 (m, 2H), 0.72 (m, 2H). Mass Spectrum (M$^{+1}$): m/z calcd. for C$_{18}$H$_{13}$ClN$_4$OS$^+$=368.05, observed m/z=369.2.

Method U (Alternate):

A mixture of chloride 22B (50 mg, 0.15 mmol) and ethanolamine (200 mL) in dioxane (4 mL) were stirred at 80° C. in a sealed vial for 18 hours. The reaction mixture was treated with H$_2$O (4 mL) and the solid isolated by filtration. The solid was taken up in a minimal amount of chloroform and purified by chromatography on silica gel eluting with hexanes/acetone mixtures. $^1$H NMR (CDCl$_3$, 400 MHz): δ 8.45 (d, 1H), 8.43 (s, 1H), 7.58 (d, 2H), 7.07 (d, 1H), 6.98 (d, 2H), 5.38 (br. s, 1H), 3.85 (s, 3H), 2.70 (m, 1H), 1.00 (q, 2H), 0.76 (m, 2H). Mass Spectrum (M$^{+1}$): m/z calcd. for C$_{19}$H$_{16}$N$_4$O$_2$S$^+$=364.10, observed m/z=365.2.

The following compounds were prepared analogously.

| No. | Compound | Molecular Formula | Calculated Mass | Observed Mass |
|---|---|---|---|---|
| 23A | | C$_{18}$H$_{13}$ClN$_4$OS | 368.05 | 369.2 |
| 23B | | C$_{19}$H$_{16}$N$_4$O$_2$S | 364.10 | 365.2 |
| 23C | | C$_{16}$H$_{11}$ClN$_4$OS | 342.03 | 343.2 |
| 23D | | C$_{17}$H$_{13}$ClN$_4$O$_2$S | 372.04 | 373.2 |

-continued

| No. | Compound | Molecular Formula | Calculated Mass | Observed Mass |
|---|---|---|---|---|
| 23E | (structure) | $C_{19}H_{18}N_4O_3S$ | 382.11 | 383.2 |
| 23G | (structure) | $C_{18}H_{16}N_4O_3S$ | 368.09 | 369.2 |
| 23H | (structure) | $C_{19}H_{16}N_4OS$ | 348.10 | 349.2 |
| 23I | (structure) | $C_{18}H_{16}N_4O_2S$ | 352.01 | 353.2 |
| 23J | (structure) | $C_{17}H_{15}N_5O_2S$ | 353.09 | 354.2 |
| 23K | (structure) | $C_{17}H_{13}ClN_4OS$ | 356.8 | 357.8 |
| 23L | (structure) | $C_{19}H_{16}N_4O_2S$ | 364.4 | 365.2 |

| No. | Compound | Molecular Formula | Calculated Mass | Observed Mass |
|---|---|---|---|---|
| 23M | | C19H14N4O2S | 362.4 | 363.2 |
| 23N | | C17H14N4O2S | 338.3 | 339.2 |
| 23O | | C17H15N5O2S | 352.41 | 353.2 |
| 23P | | C19H16N4O3S | 380.4204 | 381.2 |
| 23Q | | C17H14N4OS | 322.3 | 323.2 |
| 23R | | C18H16N4OS | 336.4 | 337.2 |

-continued

| No. | Compound | Molecular Formula | Calculated Mass | Observed Mass |
|---|---|---|---|---|
| 23S |  | C19H14N4OS | 346.40 | 347.2 |

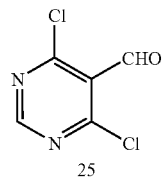

25

Method V: (Ref: A. Gomtsyan, S. Didomenico, C-H. Lee, M. A. Matulenko, K. Kim, E. A. Kowaluk, C. T. Wismer, J. Mikusa, H. Yu, K. Kohlhass, M. F. Jarvis, S. S. Bhagwat; *J. Med. Chem.*, 2002, 45, 3639-3648.)

A mixture of DMF (32 mL) and POCl$_3$ (100 mL) at 0° C. was stirred for 1 hour, treated with 4,6-dihydroxypyrimidine (25.0 g, 223 mmol), and stirred for 0.5 hour at room temperature. The heterogeneous mixture was then heated to refluxed and stirred for 3 hours. The reaction was cooled to room temperature and the resulting viscous, black liquid was poured onto ice water and extracted with diethyl ether (6×100 mL). The organic phase was subsequently washed with NaHCO$_3$, and water, dried over MgSO$_4$, and concentrated to give 25 as a yellow solid (20.0 g, 57% yield). $^1$H NMR (CDCl$_3$) δ 10.41 (s, 1H), 8.85 (s, 1H).

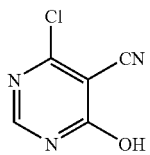

26

Method W: Step 1 (Ref: A. A. Santilli, D. H. Kim, and S. V. Wanser; J. Heterocyclic Chem., 1971, 8, 445-453.)

Aldehyde 25 (29.0 g, 164 mmoles) and hydroxylamine hydrochloride were dissolved in ACOH (0.83 M, 198 mL) by heating to reflux. The reaction was allowed to stir at reflux for 0.5 hour and then cooled to room temperature. The solvents were removed in vacuo. The resulting yellow solids were taken up in H$_2$O and the product filtered off. The solid product was then dried under vacuum overnight to provide the oxime as a yellow solid which was dried under vacuum and used crude in the next step.

Step 2; (ref: A. A. Santilli, D. H. Kim, and S. V. Wanser; J. Heterocyclic Chem., 1971, 8, 445-453)

A solution of the above oxime (5.00 g, 26.0 mmol) in thionyl chloride (104 mL) was allowed to stir at reflux for 3 hours. The reaction was cooled to room temperature and the solvents removed in vacuo. The resulting yellow-brown solid was dried under vacuum overnight to yield 26 (3.90 g, 96% yield). $^{13}$C NMR (DMSO-d$_6$) δ 164.7, 159.5, 152.3, 117.4, 102.2.

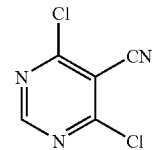

27

Method X:

To compound 26 (2.50 g, 16.0 mmoles) was added POCl$_3$ (31 mL) and Et$_3$N (2.0 mL). The reaction mixture was stirred at reflux for 3 hours and the solvents removed in vacuo. The resulting brown solid was quenched dropwise with water and basified with 40% aq. NaOH. The aqueous suspension was extracted with dichloromethane (100 ml×3), dried over MgSO$_4$ and concentrated in vacuo to provide 2.64 g of 27 as a brown solid. Mass Spectrum (M$^{+1}$): m/z calcd. for C$_7$H$_7$N$_4$Cl$^+$=183.1, found m/z=183.1.

28

Method Y: (ref: J. Clark, M. S. Shahhet, D. Korakas, G. Varvounis; *J. Heterocyclic Chem.*, 1993, 30,1065-1072.)

To compound 27 (100 mg, 0.58 mmols) and methyl thioglycolate (127 mL, 1.16 mmols) in THF (2.5 mL) was added Et$_3$N (162 μL, 1.16 mmols). The reaction immediately formed yellow precipitate and was allowed to stir for 10 minutes at room temperature. The solvents were subsequently removed in vacuo and the resulting yellow solid taken up in a minimum amount of H$_2$O. The aqueous suspension was stirred for 5 minutes and room temperature and filtered to yield 150 mg of 28 as a yellow solid. Mass Spectrum (M$^{+1}$): m/z calcd. for C$_{11}$H$_{11}$N$_3$O$_4$S$_2$$^+$=314.0, found m/z=314.0.

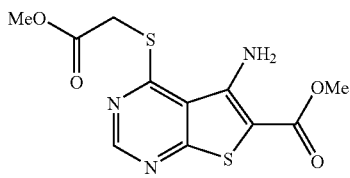

29

Method Z: (ref: J. Clark, M. S. Shahhet, D. Korakas, G. Varvounis; *J. Heterocyclic Chem.*, 1993, 30,1065-1072.)

To compound 28 (156 mg, 0.50 mmols) in toluene (3.1 mL) was added Et₃N (80 mL, 0.55 mmols). The reaction was stirred at reflux for 4 hours. The mixture was subsequently cooled to room temperature and the solvents removed in vacuo to provide 150 mg of 29 as a yellow solid. ¹H NMR (CDCl₃) δ 8.71 (s, 1H), 6.43 (bs, 2H), 4.17 (s, 2H), 3.84 (s, 3H), 3.74 (s, 3H).

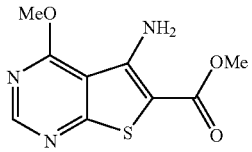

30

Method AA:

To compound 30 (37 g, 118 mmol) in methanol (500 mL) was added sodium methoxide (7.7 g, 142 mmol). The yellow suspension was heated to reflux for 4 hours. The reaction was monitored by mass spectrometry and when judged complete was cooled to 0° C., filtered, the solid washed with minimal amount of methanol and water. Drying under vacuum provided product 31 (27 g) as a white solid. ¹H NMR (CDCl₃) δ 8.66 (s, 1H), 6.48 (br. s, 2H) 4.18 (s, 3H), 3.84 (s, 3H).

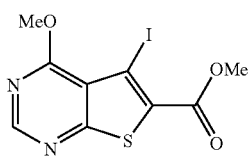

31

Method AB:

To a 60° C. solution of Iodine (86 g, 340 mmol) in CH₃CN (500 mL) were added sequentially tert-butyl nitrite (17.5 g, 170 mmol) followed by compound 30 (27 g, 113 mmol) The reaction was stirred for 1.5 hours and then poured into a solution of sodium bisulfite (600 g in 2.5 L H₂O) and stirred for 20 minutes. The resulting biphasic suspension was filtered through paper under vacuum. The solid was dried under vacuum to give 31 (20.6 g). ¹H (CDCl₃, 400 MHz): δ 8.70 (s, 1H), 4.18 (s, 1H) 3.96 (s, 1H).

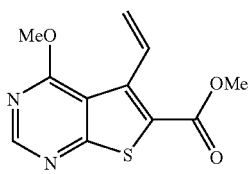

32

Method AC:

To a DMF (150 mL) solution of compound 31 (10 g, 0.40 mmol) were added tri-n-butyl-vinylstannane (13.5 mL, 0.43 mmol) and tetrakis-triphenylphosphine palladium. The reaction mixture was heated to 75° C. and stirred 96 hours. The black solution was cooled to room temperature and then transferred to a separatory funnel containing H₂O and ethyl acetate/ hexanes (4:1, 200 mL) and shaken vigorously. The layers were separated and the organic layer washed with water (3×200 mL), dried with sodium sulfate and concentrated. The crude material was stirred with hexanes and product 32 (5.2 g) isolated by filtration and was washed with a small portion of diethyl ether. ¹H NMR (CDCl₃, 400 MHz): δ 8.7 (s, 1H) 7.8 (dd, 1H), 5.7 (dd, 2h), 4.1 (s, 3H) 3.9 (s, 3H).

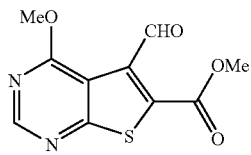

33

Method AD:

To compound 33 (5.2 g, 20.8 mmol) in THF:H₂0 (100 mL each) were added sodium periodate (22.3 g 104 mmol) and osmium tetroxide (10 mL, 1.04 mmol). The reaction mixture (suspension) was stirred for 3 hours, at which time it was quenched with sodium thiosulfate (10% aq., 50 mL). The solids were removed by filtration and the filtrate transferred to a seperatory funnel containing ethyl acetate (100 mL) and H₂O (100 mL). The layers were separated and the organic layer was extracted with chloroform (2×100 mL). The combined organics were dried over sodium sulfate and concentrated. The residue was purified by trituration with ether and the compound 33 (xx mg) was isolated by filtration and washed with hexanes. ¹H NMR (CDCl₃, 400 MHz): δ 10.62 (s, 1H) 8.75 (s, 1H) 4.15 (s, 1H) 3.98 (s, 1H).

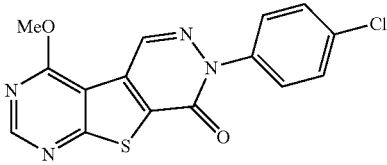

34A

Method AE:

To compound 33 (0.2 g, 0.80 mmol) in CHCl₃ (5 mL) and Methanol (5 mL) were added 4-chlorophenylhydrazine hydrochloride (0.22 g, 1.24 mmol) and aq. conc. HCl (100 mL). The dark red reaction mixture was heated to 65° C. and stirred for 18 hours. The reaction mixture was cooled to room temperature and the solvent removed. The residue was suspended in CHCl₃ (100 mL) and shaken with sodium bicarbonate (sat. aq., 100 mL). The aqueous layer as extracted with CHCl₃ (1×50 mL) and ethyl acetate (1×50 mL). The combined organics were dried over sodium sulfate and concentrated to dryness. The residue was purified by triturating with chloroform/methanol mixtures, isolated by filtration and washed with 0.5 N HCl and water. ¹H NMR (CDCl₃, 400 MHz) δ 8.88 (s, 1H), 8.81 (s, 1H), 7.68 (d, 2H), 7.48 (d, 2H), 4.32 (s, 3H).

| No. | Compound | Molecular Formula | Calculated Mass | Observed Mass |
|---|---|---|---|---|
| 34A | (structure) | C15H9ClN4O2S | 344.01 | 345.2 |
| 34B | (structure) | C16H12N4O3S | 340.06 | 341.2 |
| | (structure, labeled 35B) | | | |

Method AF:

To a solution of 34B (50 mg, 0.15 mmol) in DMSO (3 mL) was added cyclopropyl amine (200 mL, 4.25 mmol). The solution was heated to 85° C. for 16 hours, and then cooled to room temperature. The resulting solution was then slowly transferred by pipet to vigourously stirred water (25 mL). The solid 35B (34 mg) was isolated by filtration and dried in the air. 1H NMR (CDCl$_3$, 400 MHz) δ 8.77 (s, 1H), 8.37 (s, 1H), 7.56 (d, 2H), 6.98 (d, 2H), 5.72 (br. s (1H), 3.85 (s, 3H), 3.10 (m, 1H) 1.05 (q, 2H), 0.77 (m, 2H).

| No. | Compound | Molecular Formula | Calculated Mass | Observed Mass |
|---|---|---|---|---|
| 35A | (structure) | C17H15N5O2S | 353.3 | 354.2 |
| 35B | (structure) | C18H15N5O2S | 365.4 | 366.2 |

-continued

| No. | Compound | Molecular Formula | Calculated Mass | Observed Mass |
|---|---|---|---|---|
| 35C | (structure) | C17H14N4OS | 339.37 | 340.2 |

IC$_{50}$ Determination

A CHO cell line stably expressing hmGluR1 receptor was established. One day prior to assay, cells were split in growth media at concentration of 50,000 cells/well in a volume of 100 µl and seeded into black clear-bottom 96-well plates. After two to six hours, when cells were well attached to the plate, growth medium was replaced with assay medium (100 µL) consisting of DMEM high glucose, supplemented with GPT (1 U/mL) and sodium pyruvate, 1 mM. Following overnight incubation, medium was discarded and cells were loaded for 2 hours with dye from the Calcium 3 Assay Reagent Kit (Molecular Devices, # R8033), prepared according to manufacturers' instructions. A 96-tip pipettor/fluorometric imaging plate reader (FLIPR 384; Molecular Devices) was used and intracellular calcium mobilization was measured by increases in fluorescence upon agonist Quisqualate stimulation following 6 sec-baseline measurement. Test compounds were added 10 minutes before Quisqualate. IC$_{50}$ determinations for tested compounds were generated against Quisqualate 1 µM corresponding to EC$_{80}$ value in a standard dose response curve.

In the table below, those compounds having an mGluR1 IC$_{50}$ value of less than 20 nM (<20 nM) are designated with letter "A"; those with an IC$_{50}$ value of from 20 to less than 100 nM (10-<100 nM) are designated with letter "B"; those with an IC$_{50}$ value of from 100 to 1000 nM are designated with letter "C"; and those with an IC$_{50}$ value of more than 1000 nM (>1000 nM) are designated with letter "D".

| No. | Structure | mGluR1 IC$_{50}$ rating |
|---|---|---|
| 13A | (structure) | D |
| 13B | (structure) | D |
| 13C | (structure) | D |

-continued

| No. | Structure | mGluR1 IC$_{50}$ rating |
|---|---|---|
| 13D | 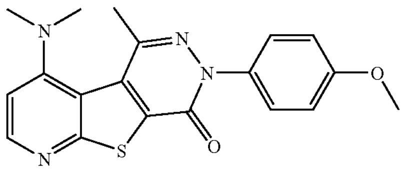 | D |
| 9A | 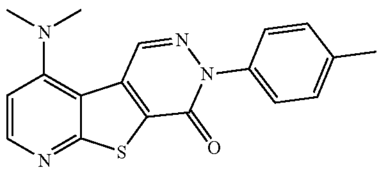 | A |
| 9C | 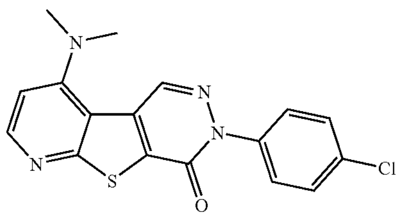 | A |
| 9D | 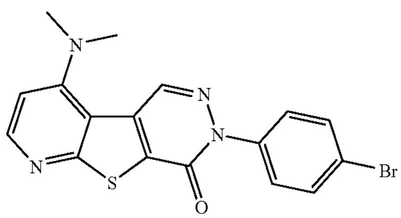 | A |
| 9F | 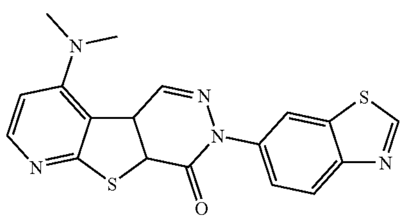 | A |
| 9B | 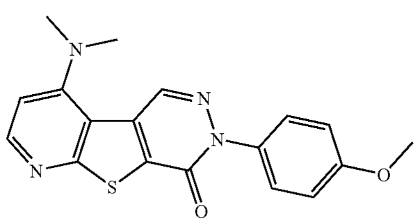 | A |
| 9G | 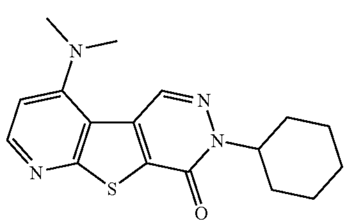 | B |

-continued

| No. | Structure | mGluR1 IC$_{50}$ rating |
|---|---|---|
| 9E | 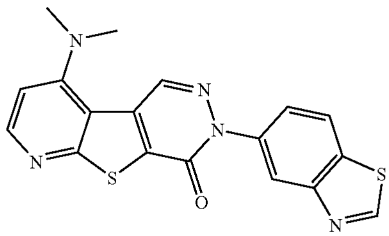 | A |
| 23D | 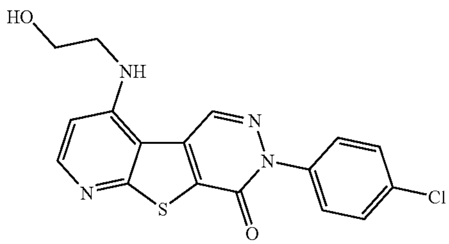 | B |
| 21B | 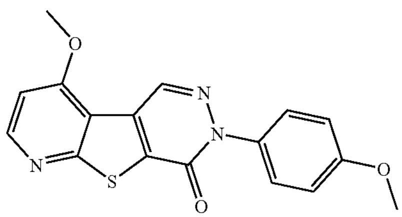 | B |
| 21C | 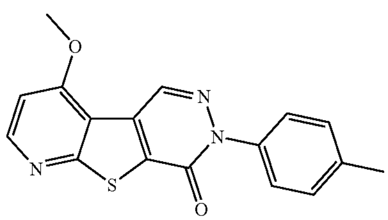 | A |
| 23A | 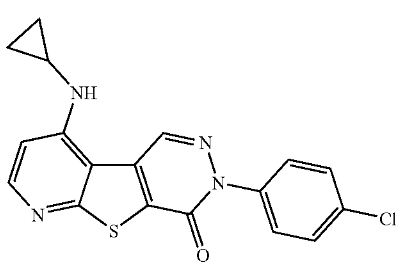 | A |
| 23C | 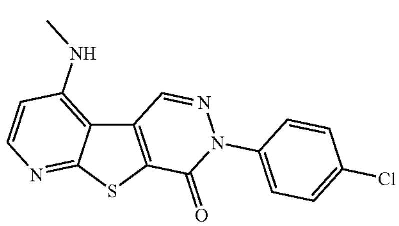 | A |

-continued

| No. | Structure | mGluR1 IC$_{50}$ rating |
|---|---|---|
| 21A | 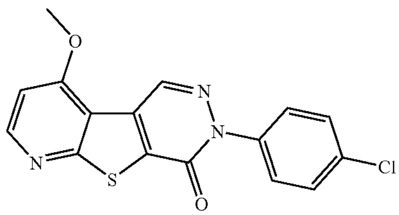 | B |
| 23H | 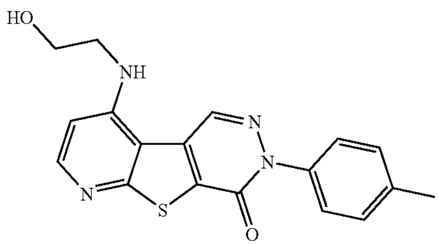 | C |
| 23G | 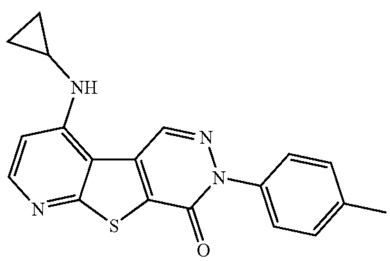 | A |
| 23E | 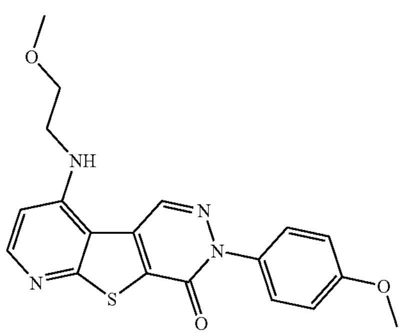 | D |
| 23B | 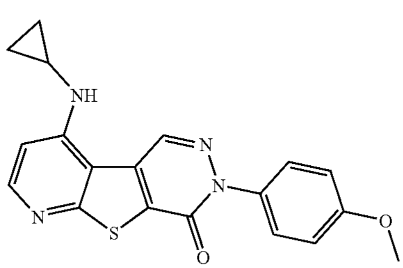 | C |

-continued

| No. | Structure | mGluR1 IC$_{50}$ rating |
|---|---|---|
| 23F | 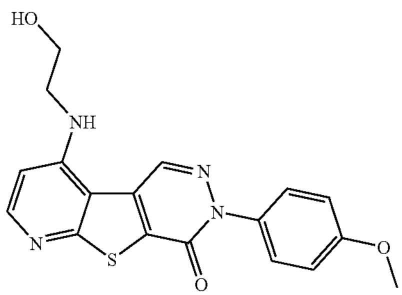 | C |
| 23I | 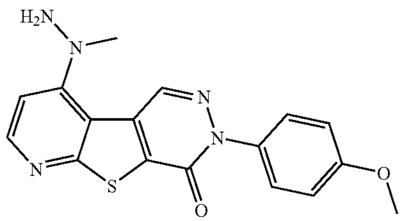 | A |
| 23J | 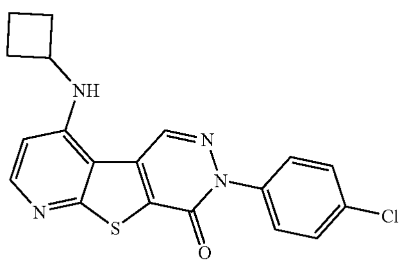 | C |
| 23K | 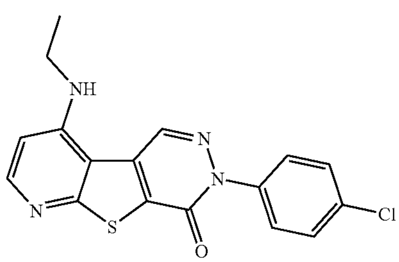 | B |
| 23L | 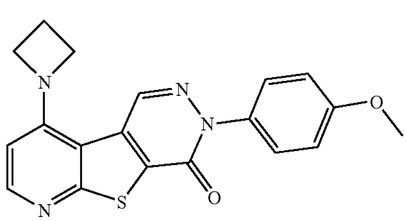 | C |
| 23M | 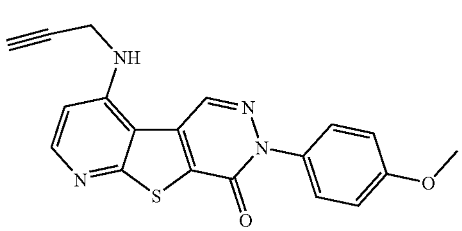 | C |

-continued

| No. | Structure | mGluR1 IC$_{50}$ rating |
|---|---|---|
| 23N | 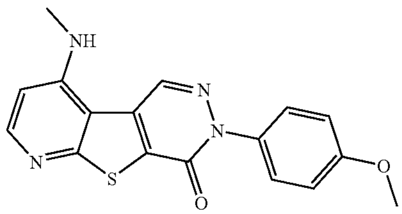 | B |
| 23O | 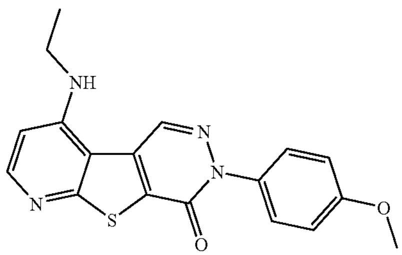 | C |
| 23P | 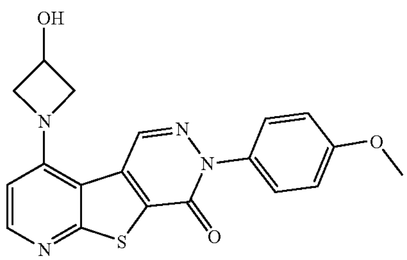 | C |
| 23Q | 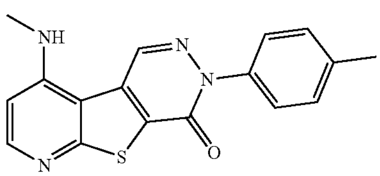 | B |
| 23R | 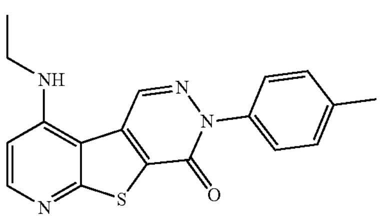 | A |
| 23S | 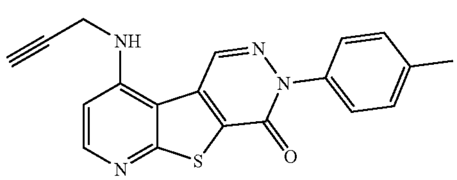 | B |
| 34B | 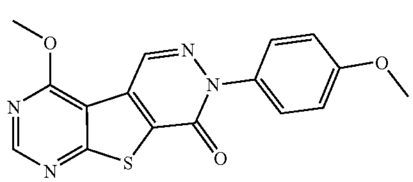 | C |

| No. | Structure | mGluR1 IC$_{50}$ rating |
|---|---|---|
| 34A | *[structure: methoxy-substituted pyrimido-thieno-pyridazinone with 4-chlorophenyl]* | B |
| 35B | *[structure: cyclopropylamino-substituted pyrimido-thieno-pyridazinone with 4-methoxyphenyl]* | B |
| 35A | *[structure: ethylamino-substituted pyrimido-thieno-pyridazinone with 4-methoxyphenyl]* | C |
| 35C | *[structure: methylamino-substituted pyrimido-thieno-pyridazinone with 4-methoxyphenyl]* | C |

Specific IC$_{50}$ values for some epresentative compounds are shown in the table below.

| Cpd # | Structure | mGluR1 IC$_{50}$ (nM) |
|---|---|---|
| 9C | *[structure: dimethylamino-substituted pyrido-thieno-pyridazinone with 4-chlorophenyl]* | 2.4 |

| Cpd # | Structure | mGluR1 IC$_{50}$ (nM) |
|---|---|---|
| 9D | 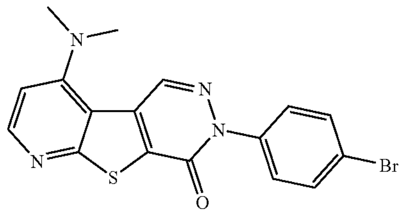 | 2.9 |
| 9A | 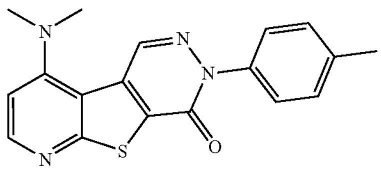 | 3.6 |
| 23I | 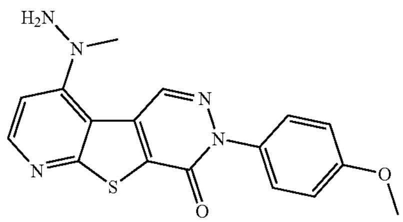 | 3.6 |
| 9E | 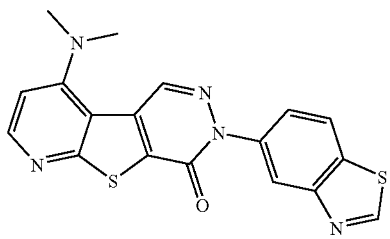 | 4.3 |
| 9B | 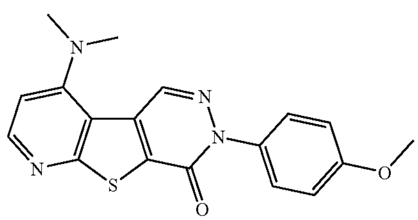 | 4.5 |
| 9F | 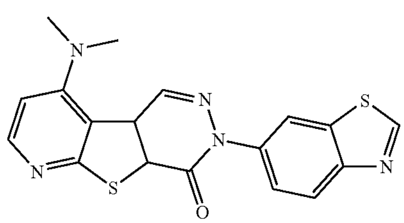 | 7.8 |
| 21C | 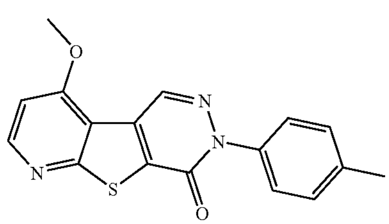 | 12.8 |

-continued

| Cpd # | Structure | mGluR1 IC$_{50}$ (nM) |
|---|---|---|
| 23A | 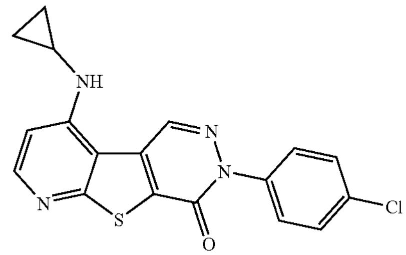 | 13.7 |
| 23R | 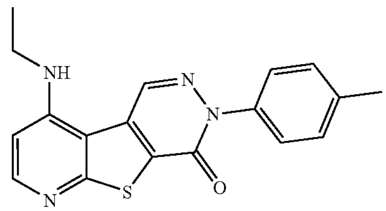 | 18.0 |
| 23G | 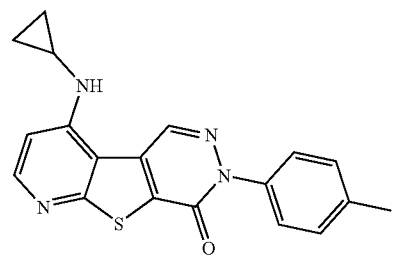 | 18.5 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:
1. A compound of formula I:

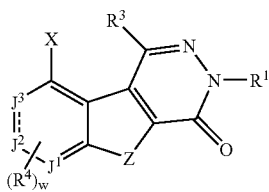

formula I or a pharmaceutically acceptable salt thereof, wherein:
$J^2$ is CH, and $J^1$ and $J^3$ are independently N or CH, provided that only 1 of $J^1$ and $J^3$ is N;
$R^1$ is selected from the group consisting of H, —NR$^5$R$^6$, —OR$^6$, —SR$^6$, —CN, —C(O)R$^6$, —C(O$_2$)R$^6$, —OC(O)R$^6$, —C(O)NR$^6$R$^7$, —N(R$^6$)C(O)R$^6$, —S(O$_2$)NR$^6$R$^7$ —N(R$^6$)S(O$_2$)R$^6$, —N(R$^6$)C(O)NR$^6$R$^7$, alkyl, alkyl substituted with at least one R$^8$ group, alkoxy, alkoxy substituted with at least one R$^8$ group, alkenyl, alkenyl substituted with at least one R$^8$ group, alkenyloxy, alkenyloxy substituted with at least one R$^8$ group, alkynyl, alkynyl substituted with at least one R$^8$ group, cycloalkyl, cycloalkyl substituted with at least one R$^8$ group, cycloalkoxy, cycloalkoxy substituted with at least one R$^8$ group, aryl, aryl substituted with at least one R$^8$ group, aryloxy, aryloxy substituted with at least one R$^8$ group, arylalkyl, arylalkyl substituted with at least one R$^8$ group, heteroaryl, heteroaryl substituted with at least one R$^8$ group, heteroarylalkyl, heteroaiylalkyl substituted with at least one R$^8$ group, heterocyclyl, heterocyclyl substituted with at least one R$^8$ group, heterocyclylalkyl and heterocyclylalkyl substituted with at least one R$^8$ group;

X is selected from the group consisting of H, —NR$^5$R$^6$, —SR$^7$, —NR$^2$NR$^5$R$^6$ —C(O)R$^6$, —SO$_2$R$^7$, —C(O)NR$^6$R$^7$, alkyl, alkyl substituted with at least one R$^8$ group, alkoxy, alkoxy substituted with at least one R$^8$ group, alkenyloxy, alkenyloxy substituted with at least one R$^8$ group, alkynyl, alkynyl substituted with at least one R$^8$ group, cycloalkyl, cycloalkyl substituted with at least one R$^8$ group, cycloalkoxy, cycloalkoxy substituted with at least one R$^8$ group, aryloxy, aryloxy substituted with at least one R$^8$ group, arylalkyl, arylalkyl substituted with at least one R$^8$ group, heteroaryl, heteroaryl substituted with at least one R$^8$ group, heteroarylalkyl, heteroarylalkyl substituted with at least one R$^8$ group, heterocyclyl, heterocyclyl substituted with at least one R$^8$ group, heterocyclylalkyl, and heterocyclylalkyl substituted with at least one R$^8$ group;

$R^3$ is selected from the group consisting of H, halo, —CN, —NO$_2$, —OR$^7$, —SR$^6$, —NR$^5$R$^6$, —C(O)R$^7$, —C(O$_2$)R$^7$, —OC(O)R$^6$, —C(O)NR$^6$R$^7$, —N(R$^6$)C(O)R$^6$, —OS(₂)R⁶, —S(O₂)R⁶, —S(O₂)NR⁵R⁶, —N(R²)S(O₂)R⁶, —N(R²)C(O)NR⁵R⁶, alkyl, alkyl substituted with at least one R⁸ group, alkoxy, alkoxy substituted with at least one R⁸ group, alkenyl, alkenyl substituted with at least one R⁸ group, alkenyloxy, alkenyloxy substituted with at least one R⁸ group, alkynyl, alkynyl substituted with at least one R⁸ group, cycloalkyl, cycloalkyl substituted with at least one R⁸ group, cycloalkoxy, cycloalkoxy substituted with at least one R⁸ group, aryl, aryl substituted with at least one R⁸ group, aryloxy, aryloxy substituted with at least one R⁸ group, arylalkyl, arylalkyl substituted with at least one R⁸ group, heteroaryl, heteroaryl substituted with at least one R⁸ group, heteroarylalkyl, heteroarylalkyl substituted with at least one R⁸ group, heterocyclyl, heterocyclyl substituted with at least one R⁸ group, heterocyclylalkyl, and heterocyclylalkyl substituted with at least one R⁸ group;

R⁴ is independently selected from the group consisting of H, halo, —CN, —NHC(O)R⁷, —NHSO₂R¹¹, —NR⁵R⁶, —OR⁷, —C(O)R⁷, —C(O₂)R⁷, —C(O)NR⁶R⁷, alkyl, alkyl substituted with at least one R⁸ group, alkoxy, alkoxy substituted with at least one R⁸ group, alkenyl, alkenyl substituted with at least one R⁸ group, alkenyloxy, alkenyloxy substituted with at least one R⁸ group, alkynyl, alkynyl substituted with at least one R⁸ group, cycloalkyl, cycloalkyl substituted with at least one R⁸ group, cycloalkoxy, cycloalkoxy substituted with at least one R⁸ group, aryl, aryl substituted with at least one R⁸ group, aryloxy, aryloxy substituted with at least one R⁸ group, arylalkyl, arylalkyl substituted with at least one R⁸ group, heteroaryl, heteroaryl substituted with at least one R⁸ group, heteroarylalkyl, heteroarylalkyl substituted with at least one R⁸ group, heterocyclyl, heterocyclyl substituted with at least one R⁸ group, heterocyclylalkyl, and heterocyclylalkyl substituted with at least one R⁸ group; or, when w=2, two adjacent R⁴, together with the carbon atoms to which they are attached, form a group of the formula:

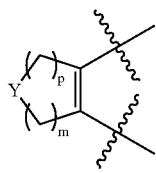

where m and p are each an integer ranging from 0-4, provided that (m+p)=2 to 7, and Y is selected from the group consisting of S, S(O), S(O)₂, O, NR⁵, C(R²)₂, and C(O);

w is an integer ranging from 1-2;

R² is selected from the group consisting of H, and alkyl;

R⁵ is selected from the group consisting of H, —C(O)R⁶, —SO₂R⁷, —C(O)NR⁶R⁷, and alkyl, alkyl substituted with at least one R⁸ group, alkenyl, alkenyl substituted with at least one R⁸ group, alkynyl, alkynyl substituted with at least one R⁸ group, cycloalkyl, cycloalkyl substituted with at least one R⁸ group, aryl, aryl substituted with at least one R⁸ group, arylalkyl, arylalkyl substituted with at least one R⁸ group, heteroaryl, heteroaryl substituted with at least one R⁸ group, heteroarylalkyl, heteroarylalkyl substituted with at least one R⁸ group, heterocyclyl, heterocyclyl substituted with at least one R⁸ group, heterocyclylalkyl, and heterocyclylalkyl substituted with at least one R⁸ group;

R⁶ and R⁷ are independently selected from the group consisting of H, alkyl, alkyl substituted with at least one R⁸ group, alkenyl, alkenyl substituted with at least one R⁸ group, alkynyl, alkynyl substituted with at least one R⁸ group, cycloalkyl, cycloalkyl substituted with at least one R⁸ group, aryl, aryl substituted with at least one R⁸ group, arylalkyl, arylalkyl substituted with at least one R⁸ group, heteroaryl, heteroaryl substituted with at least one R⁸ group, heteroarylalkyl, heteroarylalkyl substituted with at least one R⁸ group, heterocyclyl, heterocyclyl substituted with at least one R⁸ group, heterocyclylalkyl, and heterocyclylalkyl substituted with at least one R⁸ group;

or

R⁵ and R⁶ or R⁶ and R⁷, when attached to the same nitrogen atom, optionally taken together with the nitrogen atom form a 3-8 membered heterocyclic ring containing 0-3 heteroatoms independently selected from O, N or S in addition to said nitrogen atom;

each R⁸ is independently selected from the group consisting of H, halo, —OR⁹, —NO₂, —CN, —NR⁹C(O)R¹⁰, —NR⁹SO₂R¹¹, —NR⁹R¹⁰, —C(O)R¹⁰, —C(O)NR⁹R¹⁰, —C(O)OR⁹, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, wherein each said alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl of R⁸ is optionally independently unsubstituted or substituted with at least one group selected from halo, —CN, —NO₂, —OR⁶, SR⁶, —C(O)R¹⁰—NR⁹R¹⁰, —C(O₂)R⁹, —C(O)NR⁹R¹⁰, —N(R⁹)C(O)R¹⁰, —N(R⁶)C(O)NR⁹R¹⁰, and —NR⁹SO₂R¹¹;

R⁹ and R¹⁰ are each independently selected from the group consisting of H and alkyl, alkenyl, alkynyl, cycloalkyl, aryl, arylalkyl, heteroaryl, heteroarylalkyl, and heterocyclyl, wherein each said alkyl, alkenyl, alkynyl, cycloalkyl, aryl, arylalkyl, heteroaryl, heteroarylalkyl, and heterocyclyl group of R⁹ and R¹⁰ are, independently, unsubstituted or substituted with at least one group selected from halo, —CN, —NO₂, —OR⁶, —SR⁶, —NR⁵R⁶, —C(O)R⁶, —C(O²)R⁶, —OC(O)R⁶, —C(O)NR⁶R⁷, —N(R⁶)C(O)R⁶, —OS(O²)R⁶, —S(O₂)R⁶, —S(O₂)NR⁵R⁶, —N(R⁶)S(O₂)R⁶, and —N(R⁶)C(O)NR⁵R⁶; and R¹¹ is selected from the group consisting of alkyl, alkyl substituted with at least one R⁸ group, alkenyl, alkenyl substituted with at least one R⁸ group, alkynyl, alkynyl substituted with at least one R⁸ group, cycloalkyl, cycloalkyl substituted with at least one R⁸ group, aryl, aryl substituted with at least one R⁸ group, arylalkyl, arylalkyl substituted with at least one R⁸ group, heteroaryl, heteroaryl substituted with at least one R⁸ group, heteroarylalkyl, heteroarylalkyl substituted with at least one R⁸ group, heterocyclyl, and heterocyclyl substituted with at least one R⁸ group.

2. The compound of claim 1, wherein X is —NR⁵R⁶ and —NR⁵R⁶ is selected from the group consisting of

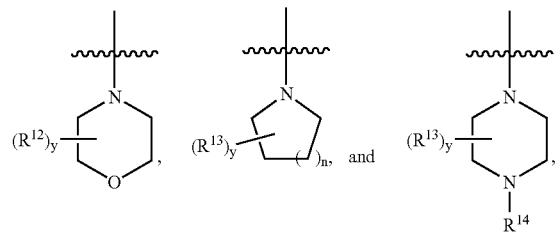

wherein
each $R^{12}$ independently is selected from the group consisting of H, —CN, —C(O)R$^6$, —C(O)OR$^7$, —C(O)NR$^6$R$^7$, alkyl, alkyl substituted with at least one R$^8$ group, alkoxy, alkoxy substituted with at least one R$^8$ group, alkenyl, alkenyl substituted with at least one R$^8$ group, alkenyloxy, alkenyloxy substituted with at least one R$^8$ group, alkynyl, alkynyl substituted with at least one R$^8$ group, cycloalkyl, cycloalkyl substituted with at least one group, cycloalkoxy, cycloalkoxy substituted with at least one R$^8$ group, aryl, aryl substituted with at least one R$^8$ group, aryloxy, aryloxy substituted with at least one R$^8$ group, arylalkyl, arylalkyl substituted with at least one R$^8$ group, heteroaryl, heteroaryl substituted with at least one R$^8$ group, heteroarylalkyl, heteroarylalkyl substituted with at least one R$^8$ group, heterocyclyl, heterocyclyl substituted with at least one R$^8$ group, heterocyclylalkyl, and heterocyclylalkyl substituted with at least one R$^8$ group;

each $R^{13}$ independently is selected from the group consisting of H, halo, hydroxyl, —CN, —NHC(O)R$^7$, —NHSO$_2$R$^{11}$, —NR$^5$R$^6$, —OR$^7$, —C(O)R$^6$, —C(O)OR$^7$, —C(O)NR$^6$R$^7$, alkyl, alkyl substituted with at least one R$^8$ group, alkoxy, alkoxy substituted with at least one R$^8$ group, alkenyl, alkenyl substituted with at least one R$^8$ group, alkenyloxy, alkenyloxy substituted with at least one R$^8$ group, alkynyl, alkynyl substituted with at least one R$^8$ group, cycloalkyl, cycloalkyl substituted with at least one R$^8$ group, cycloalkoxy, cyoloalkoxy substituted with at least one R$^8$ group, aryl, aryl substituted with at least one R$^8$ group, aryloxy, aryloxy substituted with at least one R$^8$ group, arylalkyl, arylalkyl substituted with at least one R$^8$ group, heteroaryl, heteroaryl substituted with at least one R$^8$ group, heteroarylalkyl, heteroarylalkyl substituted with at least one R$^8$ group, heterocyclyl, heterocyolyl substituted with at least one R$^8$ group, heterocyolylalkyl, and heterocyclylalkyl substituted with at least one R$^8$ group;

$R^{14}$ is selected from the group consisting of H, —C(O)R$^6$, —C(O)OR$^7$, —C(O)NR$^6$R$^7$, alkyl, alkyl substituted with at least one R$^8$ group, alkenyl, alkenyl substituted with at least one R$^8$ group, cycloalkyl, cycloalkyl substituted with at least one R$^8$ group, aryl, aryl substituted with at least one R$^8$ group, arylalkyl, arylalkyl substituted with at least one R$^8$ group, heteroaryl, heteroaryl substituted with at least one R$^8$ group, heteroarylalkyl, heteroarylalkyl substituted with at least one R$^8$ group, heterocyclyl, heterocyclyl substituted with at least one R$^8$ group, heterocyclylalkyl, and heterocyclylalkyl substituted with at least one R$^8$ group;

n is 0-4; and
y is 1-4.

3. The compound of claim 1, wherein J$^1$ is N, and J$^2$ and J$^3$ are each —CH—.

4. The compound of claim 3, wherein R$^3$ is alkyl.

5. The compound of claim 3, wherein R$^3$ is H.

6. The compound of claim 3, wherein R$^1$ is aryl.

7. The compound of claim 3, wherein R$^1$ is heteroaryl.

8. The compound of claim 3, wherein R$^1$ is p-halophenyl, and R$^3$ is H.

9. The compound of claim 1, wherein X is —NR$^5$R$^6$.

10. The compound of claim 9, wherein R$^5$ and R$^6$ are independently selected from the group consisting of hydrogen, alkyl, alkyl substituted with at least one R$^8$ group, cycloalkyl, and cycloalkyl substituted with at leastone R$^8$ group.

11. The compound of claim 9, wherein R$^5$ and R$^6$ are each alkyl.

12. The compound of claim 9, wherein R$^5$ is H and R$^6$ is alkyl which is optionally substituted with at least one substituent selected from the group consisting of —OH, alkoxy, —CF$_3$, and —C≡CH.

13. The compound of claim 9, wherein at least one of R$^5$ and R$^6$ is cycloalkyl.

14. The compound of claim 12, wherein R$^5$ is H and R$^6$ is cyclopropyl or cyclobutyl.

15. The compound of claim 2, wherein —NR$^5$R$^6$ is

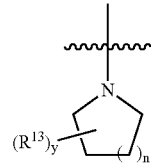

wherein n is 0.

16. The compound of claim 15, wherein R$^{13}$ is H or OH.

17. The compound of claim 9, wherein R$^1$ is selected from the group consisting of cycloalkyl and aryl, wherein each of said cycloalkyl and said aryl of R$^1$ is unsubstituted or substituted with at least one R$^8$ group.

18. The compound of claim 17, wherein said R$^1$ cycloalkyl is cyclohexyl.

19. The compound of claim 17, wherein said R$^8$ is selected from the group consisting of alkyl, cycloalkyl, cyano, alkoxy, halo, and hydroxy.

20. The compound of claim 1, wherein R$^1$ is selected from the group consisting of phenyl, phenyl substituted with at least one R$^8$ group,

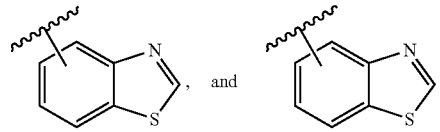

substituted with at least one R$^8$ group.

21. A compound of claim 1 having a structure according to Formula IV, or Formula V:

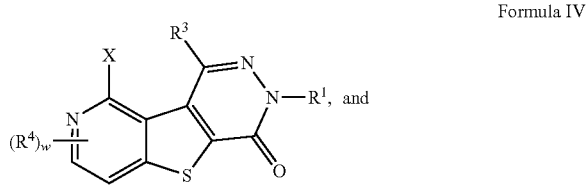

Formula IV

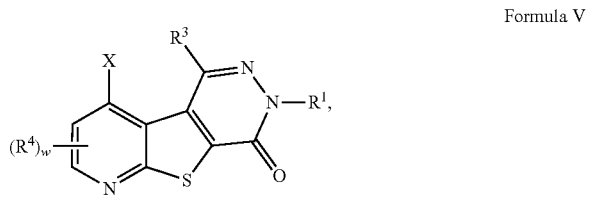

Formula V or a pharmaceutically acceptable salt thereof, wherein:
X is selected from the group consisting of H, —NR$^5$R$^6$, and —NR$^2$NR$^5$R$^6$;

R[1] is selected from the group consisting of H, phenyl, p-halophenyl, p-alkoxyphenyl, p-alkylphenyl, heteroaryl, and cycloalkyl; and
R[3] is selected from the group consisting of H and alkyl;
R[2] is selected from the group consisting of H and alkyl; and
R[5] R[6] each independently selected from the group consisting of hydrogen, alkyl, alkyl substituted with at least one R[8] group, cycloalkyl, and cycloalkyl substituted with at least one R[8] group;

wherein each of R[4] and ware as defined in claim 1.

22. A compound selected from the group consisting of those set forth below or a pharmaceutically acceptable salt thereof:

| No | Compound | No | Compound |
|---|---|---|---|
| 13A | | 13B | |
| 13C | | 13D | |
| 9A | | 9C | |
| 9D | | 9F | |
| 9B | | 9G | |
| 9E | | 23D | |

-continued
| No | Compound | No | Compound |
|---|---|---|---|
| 21B | 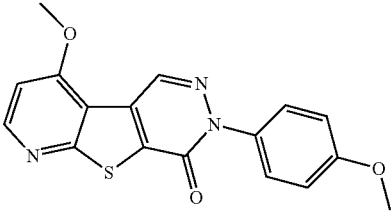 | 21C | 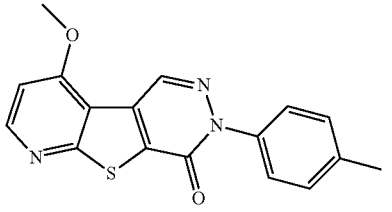 |
| 23A | 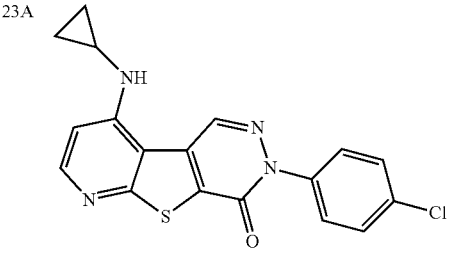 | 23C | 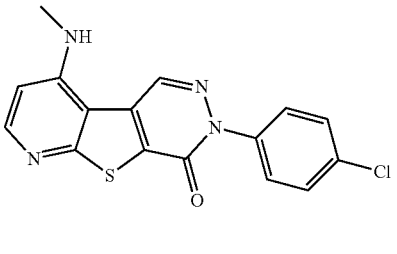 |
| 21A | 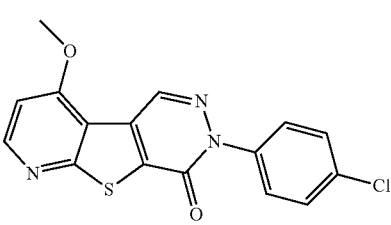 | 23H | 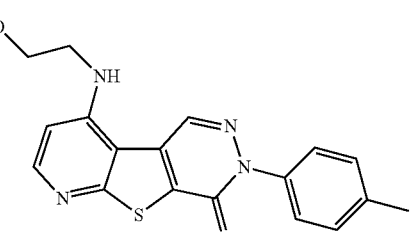 |
| 23G | 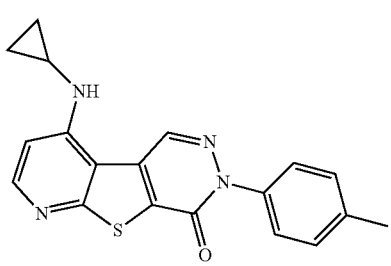 | 23E | 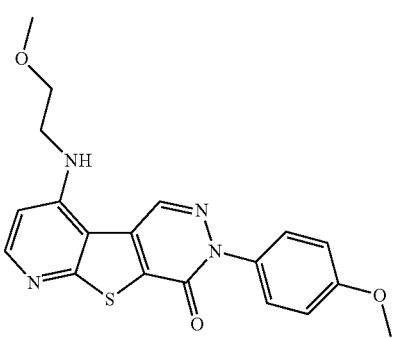 |
| 23B | 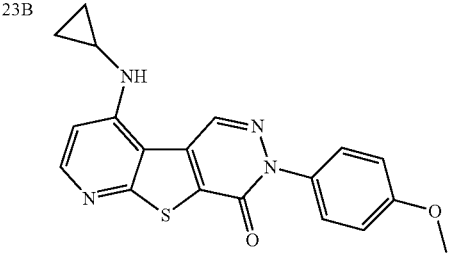 | 23F | 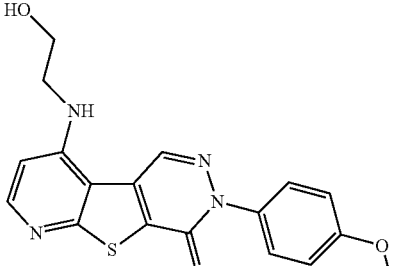 |

-continued

| No | Compound | No | Compound |
|---|---|---|---|
| 23I | | 23J | |
| 23K | | 23L | |
| 23M | | 23N | |
| 23O | | 23P | |
| 23Q | | 23R | |
| 23S | | | |

23. A pharmaceutical composition comprising at least one compound of claim 1, or a pharmaceutically acceptable salt thereof and at least one pharmaceutically acceptable carrier, adjuvant or vehicle.

24. A pharmaceutical composition comprising at least one compound of claim 22, or a pharmaceutically acceptable salt thereof and at least one pharmaceutically acceptable carrier, adjuvant or vehicle.

25. The pharmaceutical composition of claim 23, further comprising one or more additional therapeutic agents.

26. The pharmaceutical composition of claim 24, further comprising one or more additional therapeutic agents.

27. The pharmaceutical composition of claim 25, wherein said additional therapeutic agents are selected from the group consisting of therapeutic agents suitable for pain management, anti-anxiety agents, anti-migraine agents, and therapeutic agents suitable for treating urinary incontinence.

28. The pharmaceutical composition of claim 26, wherein said additional therapeutic agents are selected from the group consisting of therapeutic agents suitable for pain management, anti-anxiety agents, ant-migraine agents, and therapeutic agents suitable for treating urinary incontinence.

29. A compound of formula III:

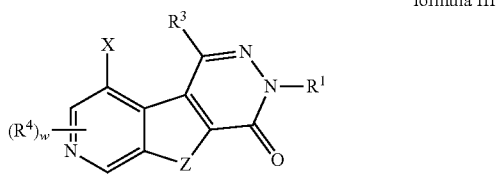

formula III or a pharmaceutically acceptable salt thereof, wherein:
$R^1$ is selected from the group consisting of H, —$NR^5R^6$, —$OR^6$, —$SR^6$, —CN, —C(O)$R^6$, —C($O_2$)$R^6$, —OC(O)$R^6$, —C(O)$NR^6R^7$, —N($R^6$)C(O)$R^6$, —S($O_2$)$NR^6R^7$ —N($R^6$)S($O_2$)$R^6$, —N($R^6$)C(O)$NR^6R^7$; and alkyl, alkyl substituted with at least one $R^8$ group, alkoxy, alkoxy substituted with at least one $R^8$ group, alkenyl, alkenyl substituted with at least one $R^8$ group, alkenyloxy, alkenyloxy substituted with at least one $R^8$ group, alkynyl, alkynyl substituted with at least one $R^8$ group, cycloalkyl, cycloalkyl substituted with at least one $R^8$ group, cycloalkoxy, cycloalkoxy substituted with at least one $R^8$ group, aryl, aryl substituted with at least one $R^8$ group, aryloxy, aryloxy substituted with at least one $R^8$ group, arylalkyl, arylalkyl substituted with at least one $R^8$ group, heteroaryl, heteroaryl substituted with at least one $R^8$ group, heteroarylalkyl, heteroartylalkyl substituted with at least one $R^8$ group, heterocyclyl, heterocyclyl substituted with at least one $R^8$ group, heterocyclylalkyl, and heterocyclylalkyl substituted with at least one $R^8$ group, or wherein said $R^1$ aryl may optionally be substituted with two radicals on adjacent carbon atoms, which radicals are taken together with the carbon atoms to which they are attached to form a five to six membered heterocyclyl or heteroaryl ring which ring is optionally substituted one at least one $R^8$;
X is selected from the group consisting of H, —$NR^5R^6$, —$SR^7$, —$NR^2NR^5R^6$ —C(O)$R^6$, —$SO_2R^7$, —C(O)$NR^6R^7$, alkyl, alkyl substituted with at least one $R^8$ group, alkoxy, alkoxy substituted with at least one $R^8$ group, alkenyloxy, alkenyloxy substituted with at least one $R^8$ group, alkynyl, alkynyl substituted with at least one $R^8$ group, cycloalkyl, cycloalkyl substituted with at least one $R^8$ group, cycloalkoxy, cyoloalkoxy substituted with at least one group, aryloxy, aryloxy substituted with at least one $R^8$ group, arylalkyl, arylalkyl substituted with at least one $R^8$ group, heteroaryl, heteroaryl substituted with at least one $R^8$ group, heteroarylalkyl, heteroarylalkyl substituted with at least one $R^8$ group, heterocyclyl, heterocyclyl substituted with at least one $R^8$ group, heterocyclylalkyl, and heterocyclyalky substituted with at least one $R^8$ group;
Z is S;
$R^3$ is selected from the group consisting of H, halo, —CN, —$NO_2$, —$OR^7$, —$SR^6$—$NR^5,R^6$, —C(O)$R^7$, —C($O_2$)$R^7$, —OC(O)$R^6$, —C(O)$NR^6R^7$, —N($R^6$)C(O)$R^6$, —$OS(O_2)R^6$, —$S(O_2)R^6$, —$S(O_2)NR^5R^6$, —N($R^2$)S($O_2$)$R^6$, and —N($R^2$)C(O)$NR^5R^6$, alkyl, alkyl substituted with at least one $R^8$ group, alkoxy, alkoxy substituted with at least one $R^8$ group, alkenyl, alkenyl substituted with at least one $R^8$ group, alkenyloxy, alkenyloxy substituted with at least one $R^8$ group, alkynyl, alkynyl substituted with at least one $R^8$ group, cycloalkyl, cycloalkyl substituted with at least one $R^8$ group, cycloalkoxy, cycloalkoxy substituted with at least one $R^8$ group, aryl, aryl substituted with at least one $R^8$ group, aryloxy, aryloxy substituted with at least one $R^8$ group, arylalkyl, arylalkyl substituted with at least one $R^8$ group, heteroaryl, heteroaryl substituted with at least one $R^8$ group, heteroarylalkyl, heteroarylalkyl substituted with at least one $R^8$ group, heterocyclyl, heterocyclyl substituted with at least one $R^8$ group, heterocyclylalkyl, and heterocyclylalkyl substituted with at least one $R^8$ group;
$R^4$ is independently selected from the group consisting of H, halo, —CN, —NHC(O)$R^7$, —$NHSO_2R^{11}$, —$NR^5R^6$, —$OR^7$, —C(O)$R^7$, —C($O_2$)$R^7$, —C(O)$NR^6R^7$, alkyl, alkyl substituted with at least one $R^8$ group, alkoxy, alkoxy substituted with at least one $R^8$ group, alkenyl, alkenyl substituted with at least one $R^8$ group, alkenyloxy, alkenyloxy substituted with at least one $R^8$ group, alkynyl, alkynyl substituted with at least one $R^8$ group, cycloalkyl, cycloalkyl substituted with at least one $R^8$ group, cycloalkoxy, cycloalkoxy substituted with at least one $R^8$ group, aryl, aryl substituted with at least one $R^8$ group, aryloxy, aryloxy substituted with at least one $R^8$ group, arylalkyl, arylalkyl substituted with at least one $R^8$ group, heteroaryl, heteroaryl substituted with at least one $R^8$ group, heteroarylalkyl, heteroarylalkyl substituted with at least one $R^8$ group, heterocyclyl, heterocyclyl substituted with at least one $R^8$ group, heterocyclylalkyl, and heterocyclylalkyl substituted with at least one $R^8$ group;
w is an integer ranging from 1-2;
$R^2$ is selected from the group of H, and alkyl;
$R^5$ is selected from the group consisting of H, —C(O)$R^6$, —S($O_2$)$R^7$, —C(O)$NR^6R^7$, alkyl, alkyl substituted with at least one $R^8$ group, alkenyl, alkenyl substituted with at least one $R^8$ group, alkynyl, alkynyl substituted with at least one $R^8$ group, cycloalkyl, cycloalkyl substituted with at least one $R^8$ group, aryl, aryl substituted with at least one $R^8$ group, arylalkyl, arylalkyl substituted with at least one $R^8$ group, heteroaryl, heteroaryl with at least one $R^8$ group, heteroarylalkyl, heteroarylalkyl substituted with at least one $R^8$ group, heterocyclyl, heterocyclylalkyl, and heterocyclylalkyl substituted with at least one $R^8$ group;
$R^6$ and $R^7$ are independently selected from the group consisting of H, alkyl, alkyl substituted with at least one $R^8$ group, alkenyl, alkenyl substituted with at least one $R^8$ group, alkynyl, alkynyl substituted with at least one $R^8$ group, cycloalkyl, cycloalkyl substituted with at least one $R^8$ group, aryl, aryl substituted with at least one $R^8$ group, arylalkyl, arylalkyl substituted with at least one $R^8$ group, heteroaryl, heteroaryl substituted with at least one $R^8$ group, heteroarylalkyl, heteroarylalkyl substituted with at least one $R^8$ group, heterocyclyl, heterocyclyl substituted with at least one $R^8$ group, heterocyclylalkyl, and heterocyclylalkyl substituted with at least one $R^8$ group; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

each $R^8$ is independently selected from the group consisting of H, halo, $-OR^9$, $-NO_2$, $-CN$, $-NR^9C(O)R^{10}$, $-NR^9SO_2R^{11}$, $-NR^9R^{10}$, $-C(O)R^{10}$, $-C(O)NR^9R^{10}$, $-C(O)OR^9$, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, wherein each said alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl of $R^8$ is optionally independently unsubstituted or substituted with at least one group selected from halo, $-CN$, $-NO_2$, $-OR^6$, $SR^6$, $-C(O)R^{10}$, $-NR^9R^{10}$, $-C(O_2)R^9$, $-C(O)NR^9R^{10}$, $-N(R^9)C(O)R^{10}$, $-N(R^6)C(O)NR^9R^{10}$, and $-NR^9S(O_2)R^{11}$;

$R^9$ and $R^{10}$ each independently selected from the group consisting of H and alkyl, alkenyl, alkynyl, cycloalkyl, aryl, arylalkyl, heteroaryl, heteroarylalkyl, and heterocyclyl groups optionally substituted with at least one of halo, $-CN$, $-NO_2$, $-OR^6$, $-SR^6$, $-NR^5R^6$, $-C(O)R^6$, $-C(O_2)R^6$, $-OC(O)R^6$, $-C(O)NR^6R^7$, $-N(R^6)C(O)R^6$, $-OS(O_2)R^6$, $-S(O_2)R^6$, $-S(O_2)NR^5R^6$, $-N(R^6)S(O_2)R^6$, and $-N(R^6)C(O)NR^5R^6$; and $R^{11}$ is selected from the group consisting of alkyl, alkyl substituted with at least one $R^8$ group, alkenyl, alkenyl substituted with at least one $R^8$ group, alkynyl, alkynyl substituted with at least one $R^8$ group, cycloalkyl, cycloalkyl substituted with at least one $R^8$ group, aryl, aryl substituted with at least one $R^8$ group, arylalkyl, arylalkyl substituted with at least one $R^8$ group, heteroaryl, heteroaryl substituted with at least one $R^8$ group, heteroarylalkyl, heteroarylalkyl substituted with at least one $R^8$ group, heterocyclyl, and heterocyclyl substituted with at least one $R^8$ group.

30. A pharmaceutical composition comprising at least one compound of claim 29, or a pharmaceutically acceptable salt thereof and at least one pharmaceutically acceptable carrier, adjuvant or vehicle.

31. The pharmaceutical composition of claim 30, further comprising one or more additional therapeutic agents.

32. The pharmaceutical composition of claim 31, wherein said additional therapeutic agents are selected from the group consisting of therapeutic agents suitable for pain management, anti-anxiety agents, anti-migraine agents, and therapeutic agents suitable for treating urinary incontinence.

* * * * *